US008809560B2

(12) United States Patent
Proctor et al.

(10) Patent No.: US 8,809,560 B2
(45) Date of Patent: Aug. 19, 2014

(54) TRANS-, TRANS-CONJUGATED LINOLEIC ACID COMPOSITIONS AND USE THEREOF

(75) Inventors: Andrew Proctor, Fayetteville, AR (US); Reddy Yettella Yenkata Ramesh, Fayetteville, AR (US); Latha Devareddy, Battle Creek, MI (US); Robert R. Beitle, Fayetteville, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 330 days.

(21) Appl. No.: 13/471,624

(22) Filed: May 15, 2012

(65) Prior Publication Data

US 2012/0295974 A1    Nov. 22, 2012

Related U.S. Application Data

(60) Provisional application No. 61/487,003, filed on May 17, 2011.

(51) Int. Cl.
| | | |
|---|---|---|
| *C11C 3/14* | (2006.01) | |
| *A23D 9/00* | (2006.01) | |
| *A01N 37/00* | (2006.01) | |
| *A61K 31/20* | (2006.01) | |
| *A23L 1/29* | (2006.01) | |
| *A61K 31/201* | (2006.01) | |
| *A23D 9/007* | (2006.01) | |
| *B01J 19/12* | (2006.01) | |
| *A23K 1/16* | (2006.01) | |
| *A23D 9/04* | (2006.01) | |
| *A23L 1/30* | (2006.01) | |
| *C11B 5/00* | (2006.01) | |

(52) U.S. Cl.
CPC ...... *A23L 1/3006* (2013.01); *B01J 2219/00103* (2013.01); *B01J 2219/0877* (2013.01); *C11C 3/14* (2013.01); *A23L 1/293* (2013.01); *A61K 31/201* (2013.01); *A23D 9/007* (2013.01); *B01J 19/127* (2013.01); *B01J 2219/00006* (2013.01); *A23K 1/164* (2013.01); *A23V 2002/00* (2013.01); *A23D 9/04* (2013.01); *B01J 2219/0011* (2013.01); *C11B 5/0035* (2013.01); *B01J 2219/0892* (2013.01)
USPC ............ 554/125; 554/126; 554/224; 514/560

(58) Field of Classification Search
USPC .......................... 554/125, 126, 224; 514/560
See application file for complete search history.

(56) References Cited

U.S. PATENT DOCUMENTS 6,127,562 A    10/2000  Cain et al.
6,153,774 A    11/2000  Seidel (Continued)

FOREIGN PATENT DOCUMENTS

EP    1097708 B1    9/2003
EP    823895 B1    7/2005

(Continued)

OTHER PUBLICATIONS

Ecker, J., G. Liebisch, W. Patsch, and G. Schmitz, The conjugated linoleic acid isomer trans-9, trans-11 is a dietary occurring agonist of liver x receptor, 2009.

(Continued)

*Primary Examiner* — Deborah D Carr
(74) *Attorney, Agent, or Firm* — Head, Johnson & Kachigian, P.C.

(57) ABSTRACT

This invention relates generally to trans-,trans-conjugated linoleic acid compositions and use thereof, and in particular to trans-,trans-conjugated linoleic acid produced from photoisomerization of soy oil in the presence of an antioxidant, and used in pharmaceutical, nutraceutical and human and animal food compositions for improved health. The invention also relates generally to a method for treatment and prevention of health-related disorders of obesity by administration of pharmaceutical, nutraceutical and/or food compositions containing and/or prepared from trans-,trans-conjugated linoleic acid-rich soy oil.

21 Claims, 21 Drawing Sheets

(56) References Cited

U.S. PATENT DOCUMENTS

| | | | |
|---|---|---|---|
| 6,440,931 | B1 | 8/2002 | Remmereit et al. |
| 6,743,931 | B2 | 6/2004 | Saebo et al. |
| 6,953,583 | B1 | 10/2005 | Ghisalberti |
| 7,101,914 | B2 | 9/2006 | Jerome et al. |
| 7,179,929 | B2 | 2/2007 | Horlacher et al. |
| 7,700,833 | B2 | 4/2010 | Renz et al. |
| 7,776,353 | B1 | 8/2010 | Saebo et al. |
| 2006/0041017 | A1 | 2/2006 | Chopra |
| 2006/0105033 | A1 | 5/2006 | Bendich |
| 2009/0042985 | A1 | 2/2009 | Bhaggan |
| 2010/0311835 | A1 | 12/2010 | Bell et al. |

FOREIGN PATENT DOCUMENTS

| | | | |
|---|---|---|---|
| EP | WO2008052709 | A2 | 5/2008 |
| EP | 1656034 | B1 | 7/2008 |
| EP | WO2009127398 | A2 | 10/2009 |
| GB | WO9813330 | A1 | 4/1998 |
| GB | WO9840059 | A1 | 9/1998 |
| JP | WO2005084661 | A1 | 9/2005 |
| JP | WO2007023588 | A1 | 1/2007 |
| MX | WO2010039019 | A1 | 4/2010 |
| WO | WO0117374 | A1 | 3/2001 |
| WO | WO0209693 | A1 | 2/2002 |
| WO | WO2008034129 | A2 | 3/2008 |

OTHER PUBLICATIONS

Adolf, R., Preparation of methyl cis-9, trans-11—and trans-9, trans-11-octadecadienoate-17, 17, 18, 18-d4, two of the isomers of conjugated linoleic acid, 2009.

Kishino, S., J. Ogawa, Y. Omura, K. Matsumura, and S. Shimizu, Conjugated linoleic acid production from linoleic acid by lactic acid bacteria, 2209.

Ogawa, J., Kishino, S., A, Ando, S. Sugimoto K. Mihara, and S. Shimizu, Production of conjugated fatty acids by lactic acid bacteria, 2005.

Coakley, M., M. C. Johnson, E. McGrath, S. Rahman, R. P. Ross, G. F. Fitzgerald, R. Devery, and C. Stanton, Intestinal bifidobacteria that produce trans-9, trans-11 conjugated linoleic acid: A fatty acid with antiproliferative activity against human colon SW480 and HT-29 cancer cells, 2005.

Macouzet, M., B. H. Lee, and N. Robert, Production of conjugated linoleic acid by probiotic *Lactobacillus acidolphilus* La-5, 2009.

Delmonte, P., J. A. G.Roach, M. M. Mossoba, G. Losi, and M. P. Yurawecz, Synthesis, isolation, and GC analysis of all the 6, 8-to 13, 15-cis/trans conjugated linoleic acid isomers, 2005.

Jain, V. P. and A. Proctor, Kinetics of photoirradiation-induced synthesis of soy oil-conjugated linoleic acid isomers, 2006.

Jain, V. P. and A. Proctor, Photocatalytic production and processing of conjugated linoleic acid-rich soy oil, 2000.

Yang, L., S. Y. V. Yeung, Y. Huang, H. Q. Wang, and Z. Y. Chen, Preferential incorporation of trans, trans-conjugated linoleic acid isomers into the liver of suckling rats, 2008.

Nichols, Jr., P. L., S. F. Herb, and R. W. Riemenschneider, Isomers of conjugated fatty acids. I. Alkali-isomerized linoleic acid, 2008.

Jain, V. P. , A. Proctor, and W. Gammill, Comparative Study of High-Linoleic Acid Vegetable Oils for the Production of Conjugated Linoleic Acid, 2010.

Jain, V. P. , A. Proctor, and T. Tokle, Effect of Minor Oil Constituents on Soy Oil Conjugated Linoleic Acid Production, 2009.

Jain, V. P. , A. Proctor, and R. Lall, Conjugated Linoleic Acid-Rich Soy Oil Tricylcylglycerol Identification, 2009.

U. Shah and A. Proctor. 2010. Separation of CLA Fatty Acid Isomers from CLA-rich Soy Oil by Reverse Phase Gradient HPLC. American Oil Chemists Annual Meeting, Phoenix, AZ, May 19, 2010.

Jain, V. P. , A. Proctor, and R. Lall, Pilot-Scale Production of Conjugated Linoleic Acid-Rich Soy Oil by Photoirradiation, 2008.

Jiang, Q., S. Christen, M. Shigenaga, and B. Ames, y-Tocopherol, the major form of vitamin E in the US diet, deserves more attention, 2001.

Gangidi, RR. and Proctor, A. 2004. Photochemical production of conjugated linoleic acid from soy oil Lipids 39:577-582, 2004.

Jain. V. and Proctor, A. 2006. Photocatalytic production and processing of conjugated linoleic rich soy oiL J. Ag & Food Chem.54:5590-5596, 2006.

Jain, V. and Proctor, A. 2007 , Kinetics of photoirradiation-induced synthesis of soy oil-conjugated linoleic acid isomers. J, Ag, & Food Chem. 55:889-894, 2007.

Jain, V. and Proctor, A. 2007 Production of conjugated linoleic acid-rich potato chips. J. Food Sci. 72:75-78.

R. T. Baublils RT, Pohlman, FW , A.H . Brown Jr. Johnson, Z.B. A. Proctor, Sawyer P. and Oias-Morse P. Galloway, D.L. 2007. Injection of conjugated linoleic acid into beef strips Meat Science 75.84-93.

Jain, V.P., Tokle, T. , Kelkar, S. and Proctor A. 2008. Effect of degree of processing on soy oil conjugalted linoleic acid yields J. Ag. Food Chem. 56:8174-8178.

Proctor, A. and Jain, V. 2009. A novel CLA Production method comes to light. Inform 20280-281.

Kadamne, J., Jain, V.P , Selah, M, Proctor, A. 2009. Measurement of conjugated linoleic acid in CLA rich oil by ATR-FTIR, J. Ag. Food Chem. 57: 10483-10488.

Kadamne, J. and Proctor, A. 2010. Rapid oil extraction from potato chips. J . Am Oil Chem Soc.87:835-836.

Kadamne, J., Castrodale, C. and Proctor, A. 2011. Measurement of Conjugated Linoleic Acid (CLA) in CLA-Rich Potato chips by ATR-FTIR Spectroscopy. J . Ag. Food Chem In press.

Rahul Lall , Vishal Jain and A. Proctor. 2009. A Rapid, Micro FAME Preparation Method for Vegetable Oil Fatty Acid Analysis by Gas Chromatography. American Oil Chemists Annual Meeting, Orlando, FL, May 6, 2009.

V. P. Jain and A. Proctor. 2005. Conjugated linoleic acid synthesis from soy oil by photo isomerization. 1FT Annual Meeting. New Orleans, LA. Jul. 19, 2005.

Tanushree Tokle, V. Jain and A. Proctor. 2009. Effect of Minor Oil Constituents on Soy Oil CLA Yields and Oxidative Stability. American Oil Chemists Annual Meeting, Orlando, FL, May 6, 2009.

A. Proctor and V.P. Jain. 2006. Production of CLA rich soy oil in the session Nutraceuticals and Bioactives in Edible Oils and their Processing Co-Products, at the American Oil Chemists Society World Conference and Exhibition on Oilseed and Vegetable Oil Utilization. Instanbul, Turkey. Aug. 16, 2006.

V. Jain and A. Proctor. 2009. Catalyst Removal from Photoirradiated Soy Oil to Obtain CLA-rich Soy Oil for Food Applications. American Oil Chemists Annual Meeting, Orlando, FL, May 6, 2009.

Jeta Kadamne, Vishal Jain and A. Proctor. 2009. ATR-FTIR Measurement of Conjugated Linoleic Acid (CLA) in CLA-rich Soybean Oil. American Oil Chemists Annual Meeting, Orlando, FL, May 4, 2009.

R. Lall, V. Jain, A. Proctor. 2008. HPLC Analysis of Triacylglycerol in CLA Enriched-Soy Oil: Role of Standards. American Oil Chemists Annual Meeting, Seattle, WA, May 19, 2008.

Shivangi Kelkar, Mi Jin Cho, A. Proctor. 2008. Oxidative Stability of Conjugated Linoleic Acid Rich Soy Oil, American Oil Chemists Annual Meeting, Seattle, WA, May 19, 2008.

W. Gilbert, V. Gadang, A. Proctor, V. Jain, L. Kalwa, and L Devareddy. 2010.The Anti-Obesity Effects of Dietary Trans-Trans Conjugated Linoleic Acid-Rich Soy Oil on Fa/Fa Obese Zucker Rats., American Oil Chemists Annual Meeting, Phoenix, AZ, May 17, 2010.

V. Jain, A. Proctor. 2008. Optimization of Pilot Scale Production of Conjugated Linoleic Acid Rich Soy Oil by Photo-Isomerization. American Oil Chemists Annual Meeting, Seattle, WA, May 19, 2008.

V. Jain, T. Tokle, S. Kelkar, A. Proctor. 2008. Conjugated Linoleic Acid Levels and Oxidation Properties of Soy Oil at Different Steps of Refining. American Oil Chemists Annual Meeting, Seattle, WA, May 19, 2008.

A. Control soy oil

B. CLA-rich soy oil

A. Control soy oil

B. CLA-rich soy oil

A. RP-HPLC fraction 3

B. RP-HPLC fraction 4

A. Control Soy oil

B. CLA-rich Soy oil

| | m | n | M | M-a | M-b | M-b-MeOH |
|---|---|---|---|---|---|---|
| 9,11,-CLA | 5 | 7 | 469 | 312 | 384 | 352 |
| 10,12-CLA | 4 | 8 | 469 | 298 | 398 | 366 |

TRANS-, TRANS-CONJUGATED LINOLEIC ACID COMPOSITIONS AND USE THEREOF

CROSS-REFERENCE TO RELATED APPLICATIONS

This application claims priority to U.S. Provisional Application Ser. No. 61/487,003, filed May 17, 2011, which is incorporated herein by reference in its entirety.

STATEMENT REGARDING FEDERALLY SPONSORED RESEARCH OR DEVELOPMENT

This invention was made with government support under grant No. 2006-35503-17539, awarded by the United Stated Department of Agriculture. The U.S. government has certain rights in the invention.

BACKGROUND OF THE INVENTION

1. Field of the Invention

This invention relates generally to trans-,trans-conjugated linoleic acid compositions and use thereof, and in particular to trans-,trans-conjugated linoleic acid produced from photoisomerization of soy oil in the presence of an antioxidant, and used in pharmaceutical, nutraceutical and food compositions for improved health. In addition, the invention relates generally to a method for treatment and prevention of health-related disorders of obesity by administration of pharmaceutical, nutraceutical and/or food compositions containing and/or prepared from trans,trans-conjugated linoleic acid-rich soy oil.

2. Description of the Related Art

Obesity, cardiovascular disease, and type 2 diabetes are international health problems with their rates predicted to rise. Research has shown that when human weight increases to the point of being classified as "obese," the risk of these health problems such as hypertension, type 2 diabetes, coronary heart disease, stroke, cancer, gallbladder disease, osteoarthritis, sleep apnea, and respiratory problems increase.

Conjugated linoleic acid (CLA) is a group of positional and geometric isomers of octadecadienoic acid with conjugated double bonds. CLA has anti-carcinogenic, anti-atherogenic, anti-diabetic and anti-obesity properties, along with the ability to increase lean body mass and to protect against immune induced body wasting disease, chronic inflammatory disease, cancer and to provide other positive health effects. The cis-9,trans-11 and trans-10,cis-12 isomers are the most common dietary forms of CLA isomers. The effects of CLA are isomer-, dose-, time-, and species-dependent. For example, the trans-10,cis-12 CLA isomer has been shown to be the more potent antiobesity agent in mice relative to other cis-9,trans-11-CLA. In another study, a diet enriched with trans-10,cis-12 CLA decreased body fat of mice to a greater extent than a diet enriched in cis-9,trans-11 CLA. In addition, treatment with trans-10,cis-12 CLA reduced the expression of several adipocyte-specific genes, including peroxisome proliferator-activated receptor-γ (PPAR-γ), a ligand-activated nuclear hormone receptor and target genes. The activity of CLA is highly isomer specific; trans-10,cis-12 CLA isomer is antiadipogenic in differentiating human preadipocytes and the cis-9,trans-11 CLA isomer promotes adipogenesis.

CLA is found naturally in dairy and beef products at levels of approximately 0.3-0.8% (w/w) of the fat as bovine rumen fermentation products. The current human intake of CLA is, however, approximately ten (10) times less than the 3 g/day minimum value recommended as being necessary to produce desirable physiological health effects, and obtaining the estimated optimum dietary CLA levels from natural beef and dairy sources would increase the total fat and saturated fat intake and increase the negative health risks associated with dietary animal fats. Therefore, a concentrated source of dietary CLA that is low in saturated fat and cholesterol is desirable.

Soy oil is the most commonly used vegetable oil in United States, and it contains about 50% linoleic acid. Other high vegetable oils high in linoleic acid include sunflower (57%), corn (55%), cottonseed (50%) and peanut (50%). High levels of CLA in vegetable oil may be produced by converting linoleic acid in to oil to CLA using photo-irradiation. Approximately 75% of total CLA's produced during linoleic photo-isomerization are trans-,trans-isomers, with the remaining being cis-,trans- and trans-,cis-isomers. Further, the degree of oil processing has an effect on CLA yields prior to the photo-irradiation step, and CLA yields increase with an increasing degree of oil refining. Moreover, Tokle, et al. (2009) determined the effect of minor soy oil components concentration on CLA yields and oxidative stability during photo-isomerization of soy oil linoleic acid, and added peroxides, phospholipids, free fatty acids and lutein all reduced CLA yields significantly, with peroxides having the greatest affect.

It is therefore desirable to provide trans-,trans-conjugated linoleic acid compositions and use thereof.

It is further desirable to trans-,trans-conjugated linoleic acid-rich soy oil compositions in order to provide significant amounts of dietary CLA in food stuffs with minimum saturated fat, calories and cholesterol.

It is still further desirable to provide a method for treatment and treatment of health-related disorders of obesity by administration of pharmaceutical, nutraceutical and food compositions containing and/or prepared from trans-,trans-conjugated linoleic acid-rich soy oil.

It is yet further desirable to provide a pharmaceutical, nutraceutical and/or food composition having increased concentrations of CLA and improved oxidative stability by addition of antioxidants to soy oil during linoleic acid photo-isomerization.

It is yet further desirable to provide a pharmaceutical, nutraceutical and/or food composition having trans-9,trans 11 and/or trans-10,trans-12-CLA produced from photoisomerization of soy oil in the presence of an antioxidant.

It is still yet further desirable to provide a food substance, a pharmaceutical and/or a nutraceutical composition containing and/or prepared from trans-9,trans 11 and/or trans-10,trans-12-CLA-rich soy oil, which is effective in reducing obesity related morbidities that are associated with an increased risk for type 2 diabetes and cardiovascular disease.

SUMMARY OF THE INVENTION

In general, in a first aspect, the invention relates to a method for enriching soy oil with conjugated linoleic acid by admixing the oil with a catalytic amount of iodine in the presence of a tocopherol to form an oil-catalyst admixture and photoirradiating the oil-catalyst admixture to produce a trans-9, trans-11- and trans-10,trans-12-CLA-rich soy oil. The iodine from the CLA-rich soy oil is then extracted, such as by using ultrafiltration. The tocopherol may be at least 1,400 ppm γ-tocopherol, particularly approximately 1,400 ppm to approximately 1,800 ppm γ-tocopherol. The CLA-rich soy oil contains approximately 75% trans-9,trans-11- and trans-10,trans-12 positional isomers of CLA. The organic solvent should be miscible with the CLA-rich soy oil, have a high iodine solubility, and be safe for use in food, nutraceutical and/or pharmaceutical processing. For example, the organic solvent is a cyclohexane:ethanol mix with about 50% to about 68% v/v ethanol, having an iodine solubility of about 24% to about 32% w/w.

In addition, the step of extracting the iodine from the CLA-rich soy oil using ultrafiltration may further include admixing the CLA-rich soy oil with an organic solvent, filtering the oil-solvent admix through a porous cellulose membrane, and collecting iodine permeate after the oil-solvent admix filters through the membrane. After filtering the oil-solvent admix through the porous cellulose membrane, the supernatant of the oil-solvent admix may be mixed with an additional about of the organic solvent to form a second oil-solvent admix. This second oil-solvent admix can then be filtered through the membrane, and then the iodine permeate may be collected after the second oil-solvent admix filters through the membrane. The filtering the oil-solvent admix and/or the second oil-solvent admix through the membrane may be performed under hydrostatic pressure from an inert gas.

In general, in a second aspect, the invention relates to a composition of a trans-9,trans-11 and trans-10,trans-12-conjugated linoleic acid isomer composition produced from photoisomerization of soy oil in the presence of γ-tocopherol and an acceptable carrier. The carrier may be a human or animal food substance, a pharmaceutically acceptable carrier or a nutraceutically acceptable carrier.

In general, in a third aspect, the invention relates to a trans-,trans-CLA composition derived from photoisomerization of soy oil and at least one antioxidant, the composition comprising a geometrical isomer composition having about 75% trans-9,trans-11-conjugated linoleic acid and trans-10, trans-12-conjugated linoleic acid, or a mixture thereof. The composition may be a pharmaceutical, nutraceutical or food composition.

In general, in a forth aspect, the invention relates to a method of treatment or prevention of obesity by administering a therapeutically effective amount of a trans-9, trans-11 and trans-10,trans-12-isomer enriched conjugated linoleic acid composition produced from photoisomerization of the composition in the presence of γ-tocopherols. The composition may be administered to a patient topically as a lotion, gel or an emulsion or administered orally as a dietary supplement or as a food ingredient. Further, the composition may be a pharmaceutical, nutraceutical or food composition.

Other advantages and features will be apparent from the following description and from the claims.

DETAILED DESCRIPTION OF THE INVENTION

The compositions and methods discussed herein are merely illustrative of specific manners in which to make and use this invention and are not to be interpreted as limiting in scope.

While the compositions and methods have been described with a certain degree of particularity, it is to be noted that many variations and modifications may be made without departing from the spirit and scope of this disclosure. It is understood that the compositions and methods are not limited to the embodiments set forth herein for purposes of exemplification.

Trans-,trans-conjugated linoleic acid compositions and use thereof, and in particular to trans-,trans-conjugated linoleic acid produced from photoisomerization of soy oil in the presence of an antioxidant, and used in pharmaceutical, nutraceutical, food and animal feed compositions for improved health is disclosed herein. Soy oil, which is high in linoleic acid and more cost effective than other high-linoleic acid oils, such as safflower oil, is photo-irradiated in order to convert linoleic acid into CLA, resulting in the oil having up to 20% CLA. The CLA isomers obtained during the photo-irradiation of soy oil are trans-trans CLA isomers, namely trans-9,trans-11 and trans-10,trans-12 positional isomers. In addition, antioxidants, such as δ-tocopherols, γ-tocopherols and/or tertiary butyl hydroquinone (TBHQ), are included to significantly increase CLA yield and improve oxidative stability of the oil during linoleic acid photo-isomerization.

Figure 1:
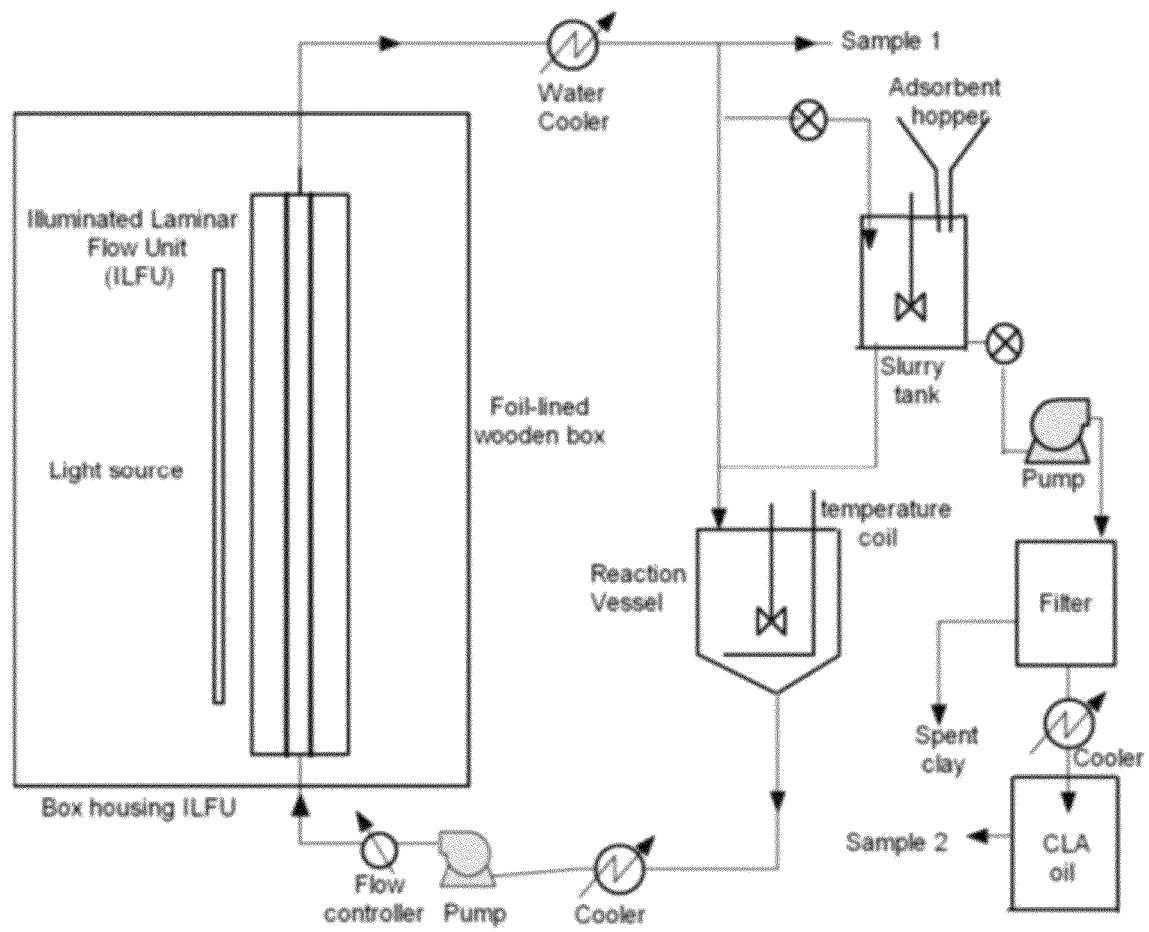
FIG. 1 is an illustration of an example of a photo-irradiation system in accordance with an illustrative embodiment of the trans-,trans-conjugated linoleic acid compositions and use thereof disclosed herein.

As exemplified in FIG. 1, soy oil is processed using a photo-irradiation system that employs a laminar flow of thin oil film to irradiate linoleic acid in the soy oil to rapidly produce trans-,trans-CLA-rich soy oil. The photo-irradiation system comprises a stainless steel reservoir with a heating unit and a stirrer, holds the oil for heating to dissolve added iodine and antioxidants prior to processing under a nitrogen blanket. The temperature of the oil can be reduced by a water heat exchanger to cool the oil with thermocouples at either side of the cooling system. The oil is then pumped into an illuminated laminar flow unit (ILFU) having two borosilicate glass places (45 cm×44 cm×0.5 cm thick) fixed in a stainless steel frame with TEFLON-coated grooves in the frame to allow laminar flow. The distance between the plates determines the thickness layer being irradiated, and is about 0.001 cm to about 10 cm, particularly about 0.5 cm. The distance is set by placing the plates in appropriate grooves within the frame. A light source, such as a tungsten halogen lamp, placed on the one side of the reaction tank ensures maximum light exposure. A light meter is placed adjacent to the light source behind a glass plate, which measures the amount of energy falling on the oil per unit time and allows calculation of oil light exposure. The internal surface of the box containing the ILFU is provided with an aluminum foil reflector to maximize light exposure. The output of the ILFU is connected to a water heat exchanger to cool the oil to 20° C. in the event the oil temperature is increased. The oil is returned to the reservoir and re-cycled until there is no further increase in the measured CLA level.

The daily recommended daily intake for iodine is about 50 to 250 μg/day, and a daily intake of about 15-70 mg of this CLA-rich oil would reach this recommended daily intake of iodine. As such, the iodine catalyst content of the CLA-rich oil is then reduced to make the CLA-rich oil more suitable for consumption by humans in food substances, nutraceuticals and/or pharmaceuticals. For example, the iodine may be extracted using an adsorption column, illustrated in FIG. 1, of 200 g non-acid activated clay (Oil Dri Corporation, Chicago, Ill.) connected parallel to the line connecting the cooler and the reservoir. On completion of the irradiation process, the oil flow is directed through the adsorption column to remove iodine and organic iodo-compounds. Oil is filtered externally to remove adsorbent and is then returned to the reservoir.

Figure 2:
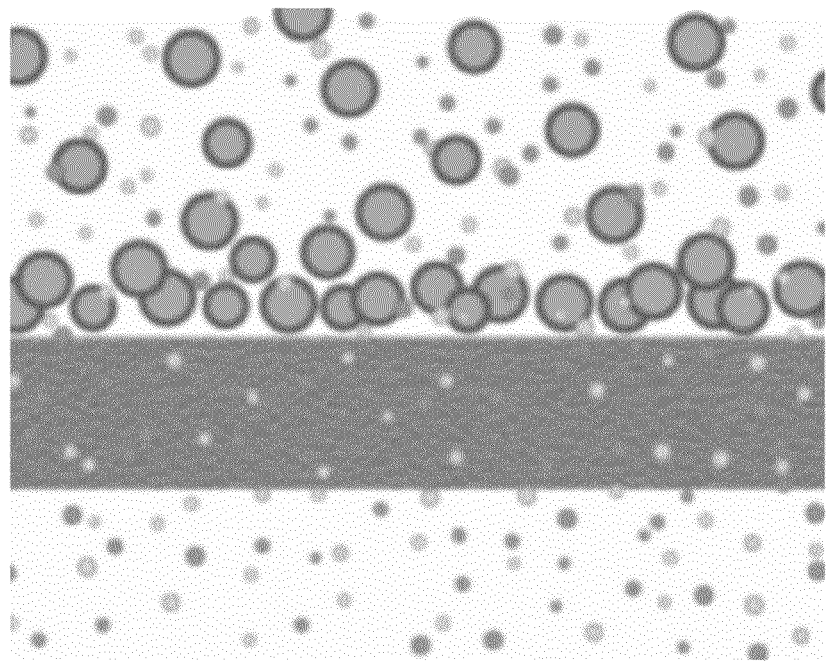
FIG. 2 is an illustration of an example of an ultrafiltration system in accordance with an illustrative embodiment of the trans-,trans-conjugated linoleic acid compositions and use thereof disclosed herein.
Figure 3:
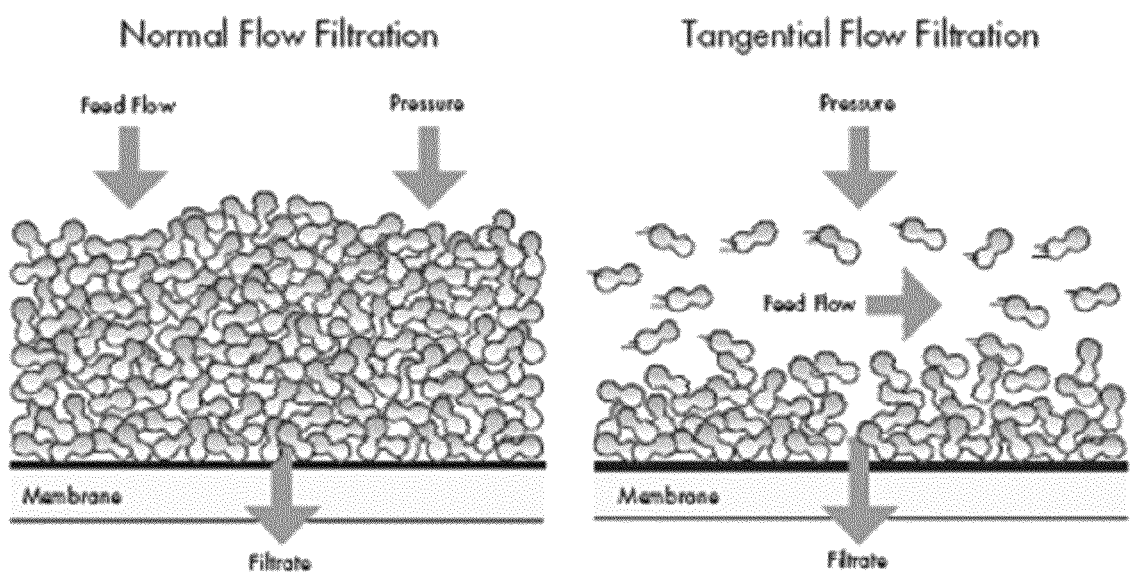
FIG. 3 is an illustration of examples of directional flow systems of the ultrafiltration system illustrated in FIG. 2.

Alternatively, the photo-irradiation system can include an ultrafiltration process to extract iodine catalyst from the oil. After the irradiation process, the oil flow is admixed with an organic solvent and directed to at least one filtration unit. As illustrated in FIG. 2, the filtration unit may have a cellulose membrane under hydrostatic pressure of a nitrogen blanket in order to force the oil through the porous cellulose membrane. Since the iodine molecules are smaller than the oil molecules, the oil molecules are retained by the membrane, while the iodine molecules pass through the membrane and out of the unit to a concentrate vessel. As illustrated in FIG. 3, the oil flow, relative to the membrane, may be either in a perpendicular direction for a batch filtration system or in a tangential direction for a continuous system of filtration. The cellulose membrane should be chemically resistant to the organic solvent so that the membrane is not damaged or destroyed during the ultrafiltration process. Additionally, the membrane should have a hydrophilic, tight microstructure to assure the highest possible retention with the lowest possible adsorption of the oil, along with the highest possible leaching of the iodine catalyst in the trans-,trans-CLA-rich soy oil. The organic solvent should be miscible with the oil, have a high iodine solubility and capable of being safely used for food, nutraceutical and/or pharmaceutical processing. For example, the organic solvent is a cyclohexane:ethanol mix with about 50% to about 68% v/v ethanol and having an iodine solubility of about 24% to about 32% w/w.

The photo-irradiation system produces about 8-20% total CLA in 12 hours, depending upon whether the oil is held statically in the ILFU (batch mode) rather than flowed through the system (continuous mode). The photo-irradiation is performed for about 30 sec to about 168 hr, particularly for about 12 hr. The soy oil is admixed with about 0.001 wt % to about 5 wt % iodine catalyst, in particular 0.35 wt %, and with an antioxidant to improve CLA yield and oxidative stability, in particular at least 1,400 ppm γ-tocopherol. The reaction temperature of the admix is maintained at about 0° C. to about 150° C., in particular 48° C.

In addition, a method for treatment and prevention of health-related disorders of obesity by administration of pharmaceutical, nutraceutical and/or food compositions containing and/or prepared from trans,trans-CLA from soy oil is disclosed herein. A diet including trans-,trans-CLA from soy oil can be administered to reduced total serum cholesterol and/or serum LDL. In addition, the trans-,trans-CLA can be administered to reduce liver weight, which is related to obesity related liver disease, to decrease glycated hemoglobin, which is a diabetes risk factor, and/or upregulated the PPAR-γ gene expression in the heart. The trans-,trans-CLA can be administered as CLA-rich soy oil or as concentrated extracts of soy oil trans-,trans-CLA isomers. It is understood that the actual amount of the trans-,trans-CLA to be administered can vary in accordance with the age, size, condition and other factors associated with the specific patient to be treated, depending upon the discretion of medical professionals.

Due to its health-promoting activities, the trans-,trans-CLA, or functional/structural variant thereof, can be incorporated as an active ingredient into pharmaceutical, nutraceutical, and food compositions for preventing or treating various obesity-related diseases. As appreciated by those skilled in the art, a nutraceutical composition refers to a food (or part of a food) that provides medical or health benefits, including the prevention and/or treatment of a disease. In this respect, not only do the disclosed nutraceutical compositions provide a nutritional source, they are also configured to provide prophylactic and therapeutic benefit against obesity-related illnesses. Accordingly, the nutraceutical compositions can be a food product, foodstuff, functional food, or a supplement composition for a food product or a foodstuff. As used herein, the term food product refers to any food or feed which provides a nutritional source and is suitable for oral consumption by humans or animals. The food product may be a prepared and packaged food (e.g., mayonnaise, salad dressing, bread, or cheese food) or an animal feed (e.g., extruded and pelleted animal feed, coarse mixed feed or pet food composition). As used herein, the term foodstuff refers to a nutritional source for human or animal oral consumption. Functional foods are foods being consumed as part of a usual diet but are demonstrated to have physiological benefits and/or reduce the risk of chronic disease beyond basic nutritional functions.

As such, the trans-,trans-CLA compositions can find use as a complete animal feed (diet), as supplement to human food products, foodstuffs, functional foods and/or animal feed, and/or as pharmaceutical formulations for enteral or parenteral applications, which may be solid formulations or liquid formulations. These compositions incorporating the trans-,trans-CLA may further contain protective hydrocolloids, such as gums, proteins, modified starches, binders, film forming agents, encapsulating agents/materials, wall/shell materials, matrix compounds, coatings, emulsifiers, foaming agents, surface active agents, solubilizing agents, e.g., oils, fats, waxes, lecithins etc., adsorbents, carriers, fillers, co-compounds, dispersing agents, wetting agents, processing aids (solvents), flowing agents, flavoring agents, sweetening agents, coloring agents, weighting agents, jellyfying agents, gel forming agents, anti-oxidants, anti-microbial and other preservative agents.

Moreover, a multi-vitamin and mineral supplement may be added to the compositions incorporating the trans-,trans-CLA to obtain an adequate amount of an essential nutrient, which is missing in some diets. The multi-vitamin and mineral supplement may also be useful for disease prevention and protection against nutritional losses and deficiencies due to lifestyle patterns. In addition, the compositions having the trans-,trans-CLA may be incorporated into beverages, e.g., non-alcoholic and alcoholic drinks, soft drinks, sport drinks, energy drinks, fruit juices, lemonades, teas and milk-based drinks, along with other dairy products and/or fortified food and bakery goods.

Further, the pharmaceutical, nutraceutical and food compositions may be in any galenic formulation that is suitable for administrating to the human body or to a suitable animal species, especially in any form that is conventional for oral administration, e.g., in solid form such as (additives/supplements for) food or feed, food or feed premix, fortified food or feed, tablets, pills, granules, capsules, and effervescent formulations, such as powders and tablets, or in liquid form, such as solutions, emulsions or suspensions, e.g., beverages, pastes and oily suspensions. The pastes may be filled into hard or soft shell capsules, whereby the capsules feature, e.g., a matrix of (fish, swine, poultry, cow) gelatin, plant proteins or ligninsulfonate. Examples for other acceptable forms of administration are transdermal, parenteral and injectable. The pharmaceutical, nutraceutical and food compositions may be in the form of controlled immediate or sustained release formulations.

EXAMPLES

The trans-,trans-CLA and use thereof disclosed herein is further illustrated by the following examples, which are provided for the purpose of demonstration rather than limitation.

Example 1

Extraction of Iodine from CLA-Rich Soy Oil Using Ultrafiltration

Eight (8) 25 ml CLA-rich soy oil samples were taken and mixed with 50 mL of ethanol:cycloyhexane (50:50 v/v) extraction solvent. Four (4) of the samples were stirred at 340 rpm, while the other four (4) samples were stirred at 860 rpm, under nitrogen gas of 40 psi and 80 psi, for 24 hr. The oil content in both permeate and concentrate were analyzed by evaporating the solvent from a sample under reduced pressure. The oil content was then obtained from the mass difference, and the iodine concentrate was determined by UV-Vis spectrometry and titration with thio sulfate.

A PLBC membrane having a NMWL of 3 kDa resulted in a permeate oil content of about 6% to about 10% w/w, resulting in about 4.5% to about 7% loss in oil during the filtration process.

TABLE 1

Iodine Extraction Yield

| Pressure (psi) | Stir Speed (rpm) | Iodine Extracted (%) | Permeate Vol. (mL) |
|---|---|---|---|
| 40 | 340 | 9.4 | 20 |
| 80 | 340 | 11.8 | 22 |
| 40 | 860 | 4.7 | 15 |
| 80 | 860 | 1.2 | 20.5 |

A PLAC membrane having a NMWL of 1 kDa resulted in a permeate oil content of about 0.5 to about 2%, resulting in only about 0.3 to about 0.7% loss during filtration.

TABLE 2

Iodine Extraction Yield

| Pressure (psi) | Stir Speed (rpm) | Iodine Extracted (%) | Permeate Vol. (mL) |
|---|---|---|---|
| 40 | 340 | 11.1 | 6 |
| 80 | 340 | 7.0 | 15 |
| 40 | 860 | 13.1 | 5 |
| 80 | 860 | 6.0 | 12.5 |

Filtration with the PLAC cellulose membrane results in less CLA-rich oil loss than the larger PLBC membrane, and extracted more iodine remaining in the oil after photoisomerization.

A difiltration was also conducting by passing two (2) successive extractions through a PLAC cellulose membrane under 80 psi of nitrogen pressure while stirred at 340 rpm. After the first iodine extraction, an additional 25 mL of organic solvent was added to the oil permeate, which was then processed again using the ultrafiltration method.

TABLE 3

Iodine Extraction Yield

|  | Iodine Extraction Yield (%) | Oil Loss (%) | Permeate Vol. (mL) |
|---|---|---|---|
| 1$^{st}$ Extraction | 3.2 | 0.68 | 15 |
| 2$^{nd}$ Extraction | 19.6 | 0.42 | 7 |

The two-step difiltration method resulted in about 22% of the iodine catalyst from the photoirradiation being extracted, with only about 1% oil lost.

Example 2

Increased Production of trans-,trans-CLA-Rich Soy Oil Using Synthetic Antioxidants and Mixed Tocopherols Soy oil (Riceland Foods, Stuttgart, Ark.) was heated in 1 L beaker to 70° C. while flushing with nitrogen to avoid oxidation. Then, 0.35% resublimed iodine crystals (EM Science, Cherry Hill, N.J.) were added to the oil, and the contents in the beaker were stirred until the iodine was completely dissolved. Twenty six (26) 50 g oil samples were taken from the oil and iodine solution, and antioxidants ascorbyl palmitate (AP), butylated hydroxy anisole (BHA), butylated hydroxy toluene (BHT), tertiary butyl hydroquinone (TBHQ) (Sigma-Aldrich, St. Louis, Mo.) and mixed tocopherols (Riceland Foods, Stuttgart, Ark.) were added to obtain a range of oil samples having antioxidant concentrations described below in Table 4.

TABLE 4

Antioxidant Concentrations

| Combination | Concentration (ppm) | | | | |
|---|---|---|---|---|---|
|  | BHA | BHT | TBHQ | AP | MT |
| 1 | 100 | — | — | — | — |
| 2 | 200 | — | — | — | — |
| 3 | — | 100 | — | — | — |
| 4 | — | 200 | — | — | — |
| 5 | 50 | 50 | — | — | — |
| 6 | 100 | 100 | — | — | — |
| 7 | — | — | 100 | — | — |
| 8 | — | — | 200 | — | — |
| 9 | — | — | 50 | 50 | — |
| 10 | — | — | 100 | 100 | — |
| 11 | — | — | — | — | 1400 |
| 12 | — | — | — | — | 1600 |
| 13 | — | — | — | 250 | 1400 |
| 14 | — | — | — | 500 | 1600 |

Synthetic antioxidants were tested at or below legal limits of usage in foods (200 ppm) and mixed tocopherols were tested at higher concentrations since their usage in foods is unregulated. Three (3) 5 g samples taken from 50 g oil aliquots, were placed in 7 mL borosilicate vials. These vials were photo-irradiated. The vials were attached to the glass plate of the photo-isomerization unit on the oil side at locations that provided uniform and maximum UV intensity. Irradiation was carried out for 12 h at 47° C.

Methyl esters were prepared from refined, bleached and deodorized (RBD) soy oil (Riceland Foods, Stuttgart, Ark.) and photo-isomerized oil by a base-catalyzed method to reduce the formation of conjugated trans,trans isomers during analysis. One hundred milligrams (100 mg) of photo-isomerized soybean oil was weighed into a 25 mL centrifuge tube and 500 μL of 1% heptadecanoic acid methyl ester (17:0, internal standard, Sigma-Aldrich, St. Louis, Mo.), 2 mL of toluene, and 4 mL of 0.5M sodium methoxide (EMD Chemicals, Darmstadt, Germany) in methanol were added to the centrifuge tube and then purged with nitrogen gas. The centrifuge tube was heated to 50° C. for 10 to 12 min and then cooled for 5 min. To inhibit formation of sodium hydroxide, which could hydrolyze methyl esters to free fatty acids, 200 μL of glacial acetic acid was added to the centrifuge tube. Five milliliters (5 mL) of distilled water was added to the centrifuge tube followed by 5 mL of hexane, and the tube was vortexed (Model VM-3000, VWR, Thorofare, N.J.) for 2 min. The hexane layer was extracted and dried over anhydrous sodium sulfate (EMD Chemicals, Darmstadt, Germany) in a 7 mL glass vial. Another 5 mL of hexane was added to the centrifuge tube, the tube was vortexed for another 2 min, and the hexane layer was dried over anhydrous sodium sulfate prior to methyl ester analysis.

Methyl esters were analyzed by gas chromatography (GC) using an SP 2560 fused silica capillary column (100 m×0.25 mm i.d.×0.2 μm film thickness; Supelco Inc., Bellefonte, Pa.) with a flame ionization detector (FID) (Model 3800, Varian, Walton Creek, Calif.). Duplicate 2 μL samples, prepared in hexane, were injected by an autosampler CP8400 (Varian) and gas chromatograms were collected by Galaxie Chromatography Workstation 1.9.3.2 (Varian). Commercial CLA methyl esters (Sigma-Aldrich, St. Louis, Mo.) containing a mixture of cis-9,trans-11 CLA, trans-10,cis-12 CLA, and trans-,trans-CLA isomers were used as a standard and heptadecanoic acid methyl ester (17:0; Sigma-Aldrich) were used as the internal standard. Two (2) determinations each consisting of duplicate injections were conducted for each treatment.

CLA concentrations were calculated by the following equation:

$$\text{Isomer } conc. = \frac{\begin{bmatrix} \text{internal standard } conc.(5\text{ mg}) \times \\ \text{peak area} \times \text{relative response factor} \end{bmatrix}}{\text{internal standard peak area}} \quad \text{(Eq. 1)}$$

An AOCS acetic acid-choloroform method (AOCS Cd 8-53) was used to measure the oxidation in the oil samples (AOCS 1998). Peroxide value (PV) of RBD soy oil and photo-isomerized oil samples were measured in duplicate.

Analysis of variance (ANOVA) was conducted on all data using JMP version 5.0.1 (SAS Institute Inc., Cary, N.C.). A student t test was used to differentiate mean values, with significant defined at p<0.05. Standard deviations were also determined.

Figure 4:
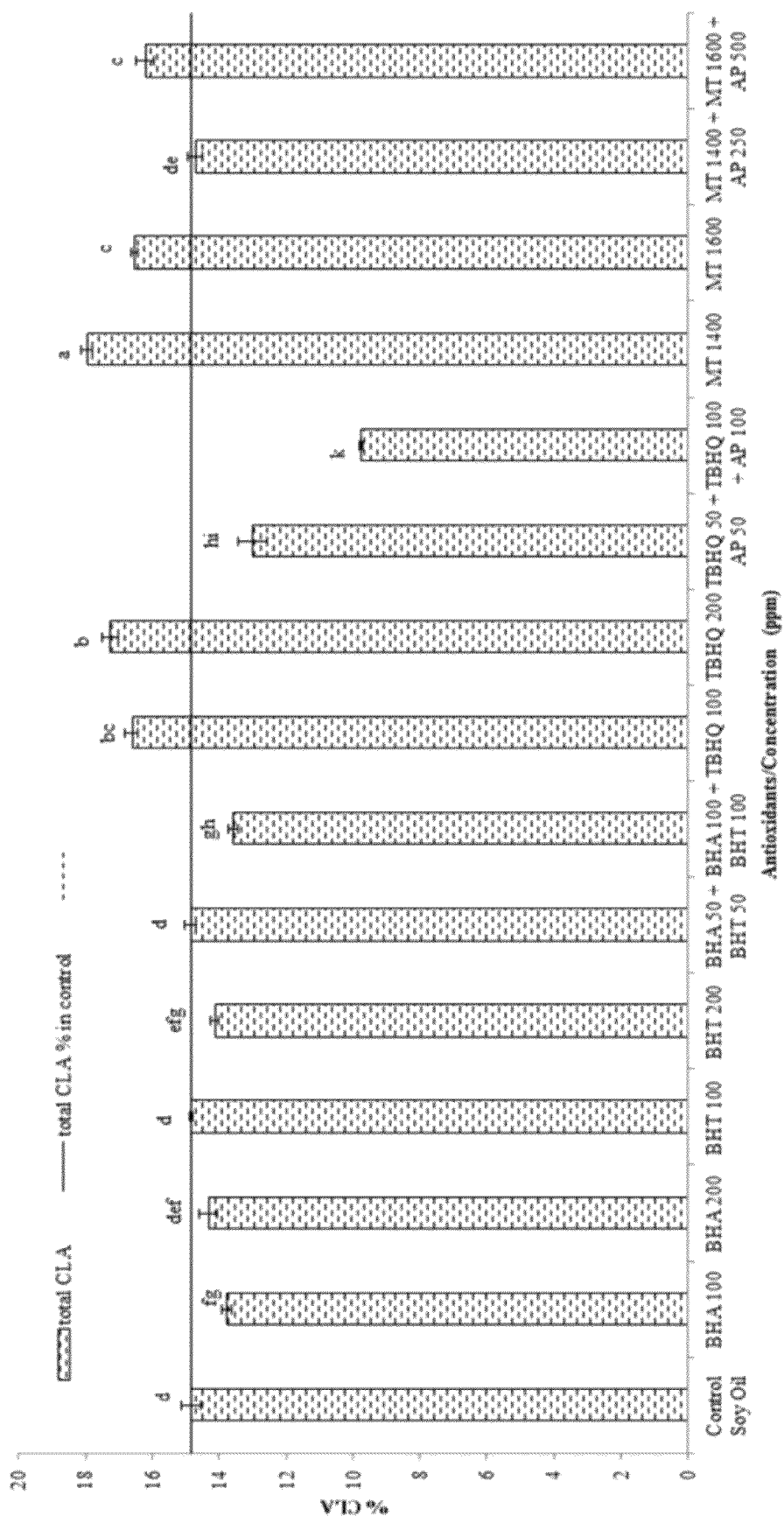
FIG. 4 is a graphical illustration of CLA yields obtained by photo-isomerization of soy oil linoleic acid with oils of various added antioxidants, where error bars represent standard error of mean (n≥4) and means with different letters are significantly different at p<0.05.

FIG. 4 shows soy oil total CLA yields with various antioxidant additions at different concentrations. The control RBD soy oil produced 14.8% total CLA after 12 hours of irradiation, while BHA, BHT and BHT/BHA combinations either did not affect CLA yields or significantly reduced it. TBHQ, MT, and MT with 500 ppm AP at much higher concentration than BHA and BHT, however, showed significantly greater CLA yields relative to control RBD soy oil (p<0.05). The largest CLA yield was 18%, obtained with 1400 ppm MT and was significantly greater than all other treatments. As further illustrated in FIG. 4, increasing MT to 1600 ppm and addition of AP to MT reduced CLA yields, but they were still greater than the control. TBHQ is more effective than BHT and BHA at similar concentrations as biphenol and BHT and BHA are monophenols.

Figure 5:
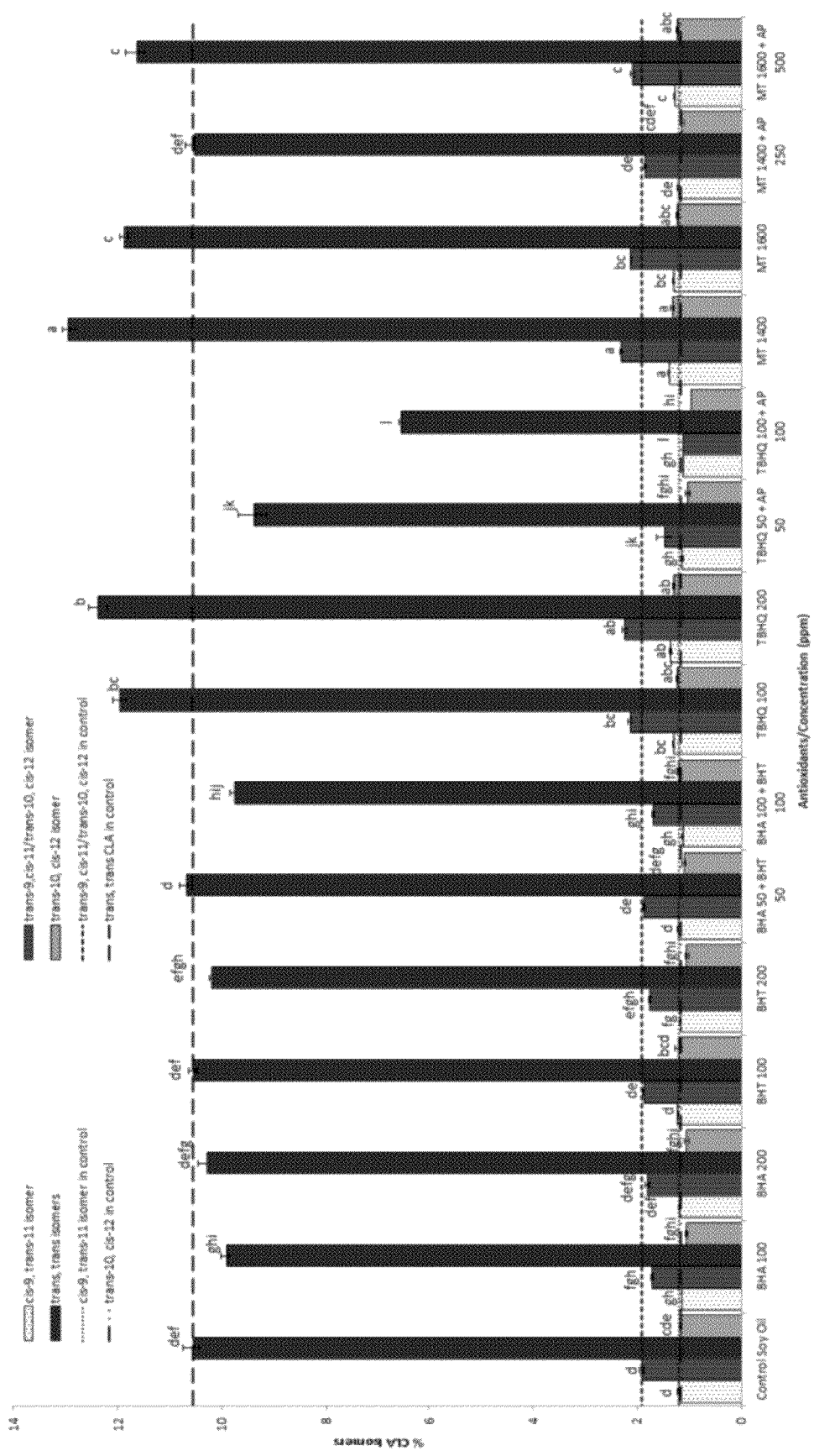
FIG. 5 is a graphical illustration of CLA isomer yields obtained by photo-isomerization of soy oil linoleic acid with oils of various added antioxidants, where error bars represent standard error of mean (n≥4) and means with different letters are significantly different at p<0.05.
Figure 10:
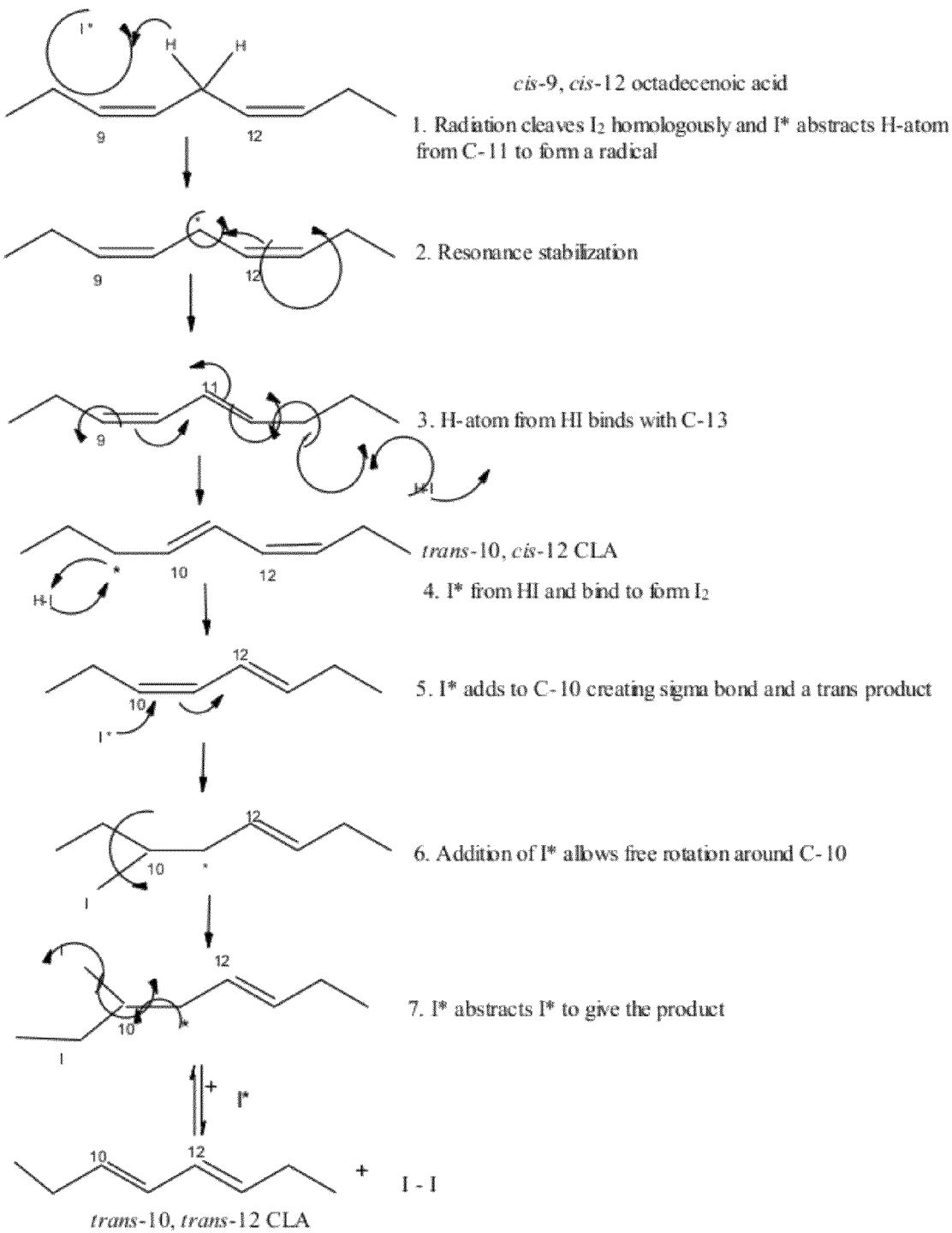
FIG. 10 is a schematic illustration of the mechanism for the formation of CLA isomers during photo-isomerization of soy oil in accordance with an illustrative embodiment of the trans-,trans-conjugated linoleic acid compositions and use thereof disclosed herein.

The relative amount of each CLA isomers obtained with each antioxidant treatment is illustrated in FIG. 5. The major CLA isomer produced during photoirradiation is the trans-,trans-CLA isomer, whose production relative to control levels is similar to total CLA. Other cis-,trans- and trans-,cis-CLA isomers are at about 1-2% levels because CLA isomerizes to the more thermodynamically stable trans-,trans-CLA during processing, as illustrated in FIG. 10. Processing treatments that result in reduced total CLA and trans-,trans-CLA, the minor isomers are not proportionally reduced, as can be seen when reduced trans-,trans-CLA isomer contents of 'TBHQ-100+AP 100' treatment is compared with that of 'MT 1400'.

Figure 6:
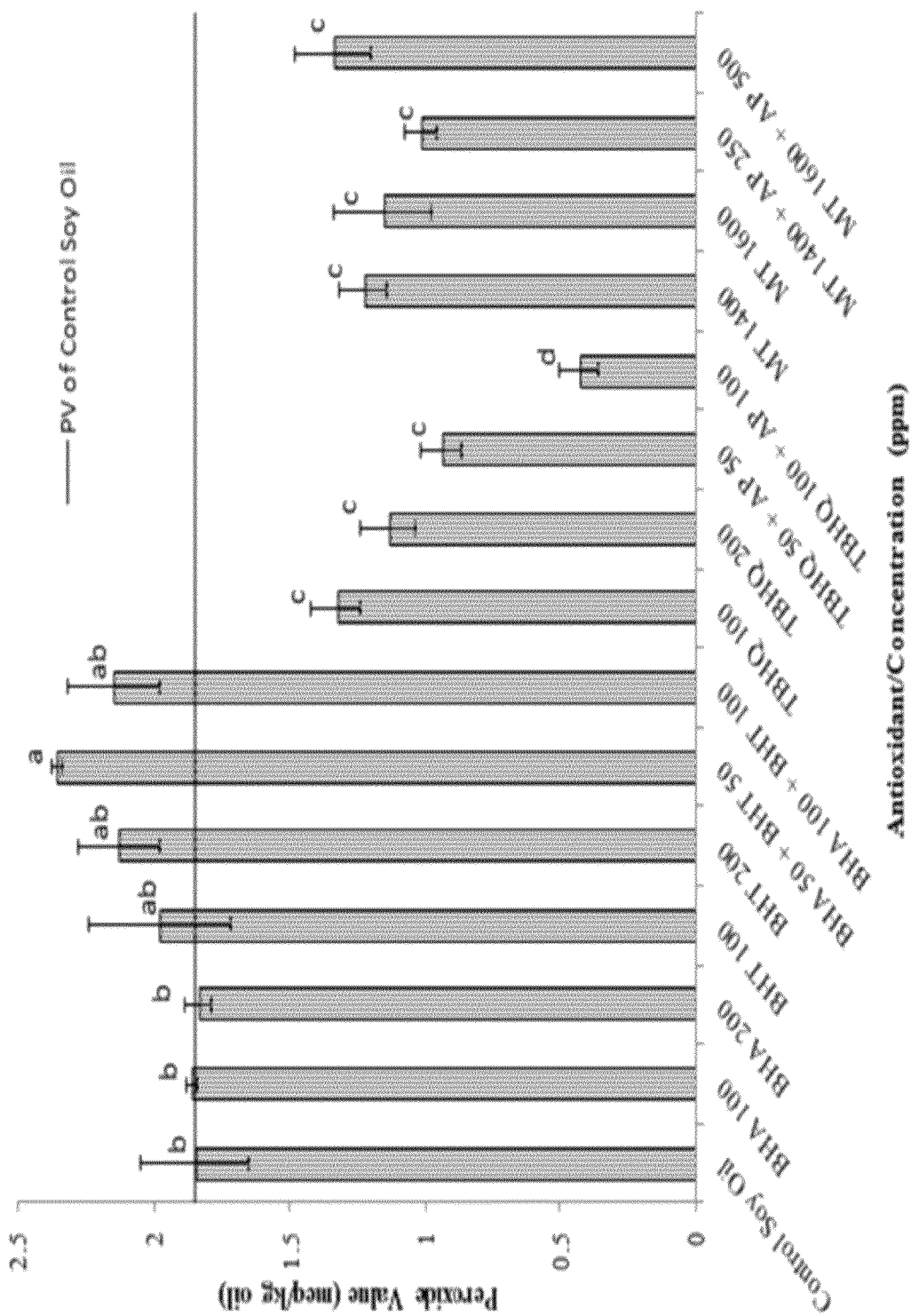
FIG. 6 is a graphical illustration of peroxide values of photo-isomerized soy oil with various added antioxidants, where error bars represent standard error of mean (n≥4)

FIG. 6 shows the peroxide values after photoisomerization of soy oil linoleic acid with various antioxidant treatments. The PV of control soy oil after 12 hours of irradiation was 1.85 meq/kg of oil. The PV of soy oil with TBHQ and MT treatments either alone or in combination with AP significantly lowered the PV relative to the control. The soy oil PV with BHA and BHT either alone or in combination did not affect PV or resulted in a slight increase. Generally, the increase in oxidation stability was greatest in those samples with most CLA content, however, MT produced the highest CLA yields (FIG. 4), although 'TBHQ 100+AP 100' treatment produced a significantly lower PV value than the other treatments.

Example 3

Effect of α-, γ- and δ-Tocopherol on Yield and Oxidative Stability of trans-,trans-CLA-Rich Soy Oil In order to determine the effect of α-, γ- and δ-tocopherols on CLA yields and oxidative stability, oil samples were prepared with 600, 1000, 1400 and 1800 ppm of α-tocopherols (TCI America, Portland, Oreg.) and γ- and δ-tocopherols (Sigma-Aldrich, St. Louis, Mo.), as illustrated below in Table 5.

TABLE 5

α-, γ- and δ-Tocopherol Concentrations

| Combination | Concentration (ppm) | | |
|---|---|---|---|
| | α-tocopherol | γ-tocopherol | δ-tocopherol |
| 1 | 600 | — | — |
| 2 | 1000 | — | — |
| 3 | 1400 | — | — |
| 4 | 1800 | — | — |
| 5 | — | 600 | — |
| 6 | — | 1000 | — |
| 7 | — | 1400 | — |
| 8 | — | 1800 | — |
| 9 | — | — | 600 |
| 10 | — | — | 1000 |
| 11 | — | — | 1400 |
| 12 | — | — | 1800 |

The oil samples were irradiated for 12 h using the photo-irradiation system. The CLA content of the samples was then analyzed by GC-FID and oxidative stability was measured by PV, also similarly to above.

Figure 7:
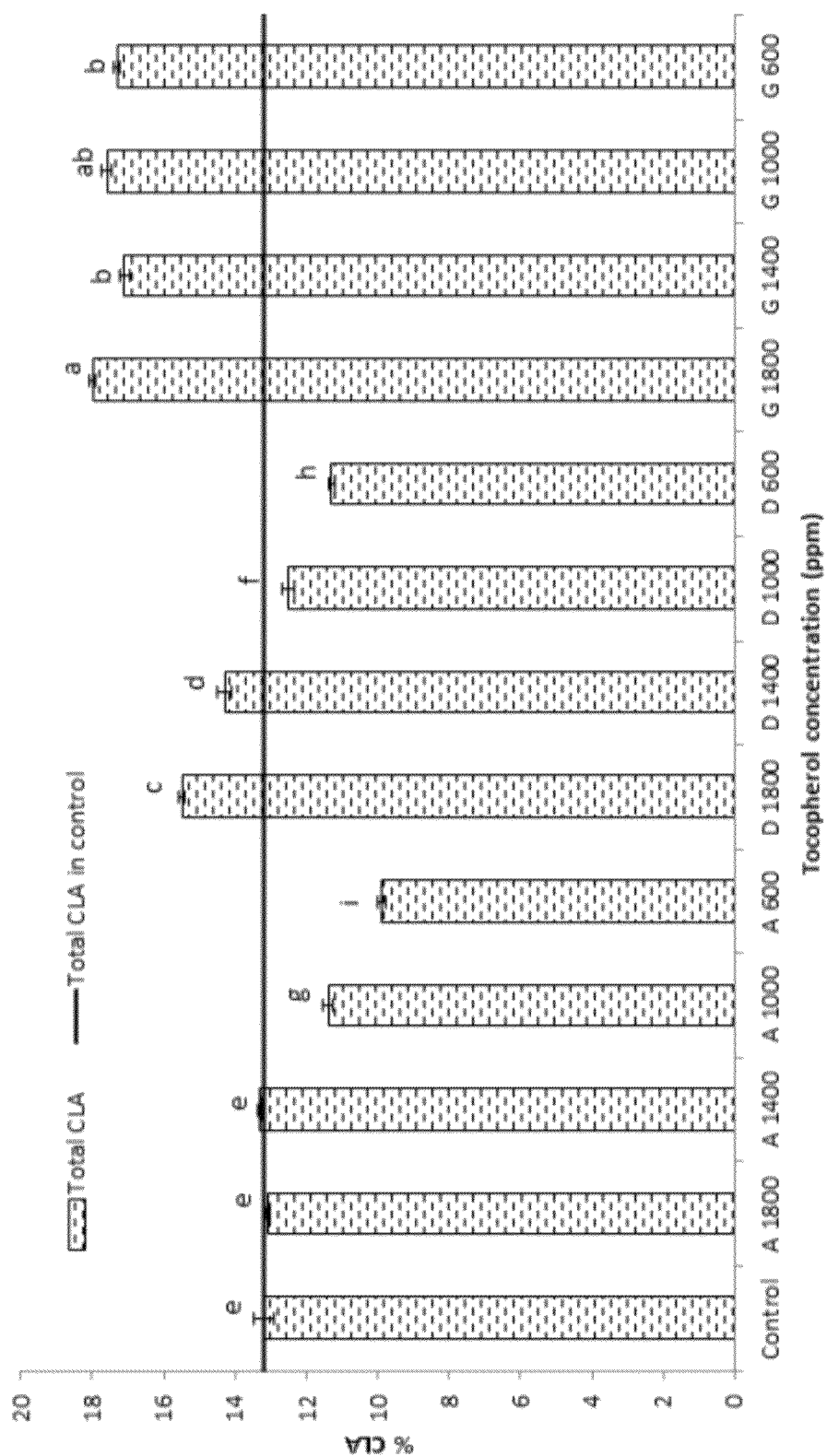
FIG. 7 is a graphical illustration of CLA yields obtained by photo-isomerization of soy oil linoleic acid with oils of various concentrations of α-, γ- and δ-tocopherols, where error bars represent standard error of mean (n≥4) and means with different letters are significantly different at p<0.05.

FIG. 7 shows the total soy oil CLA content obtained with various concentrations of α-, γ- and δ-tocopherols relative to a control. The γ-tocopherols at all concentrations produced significantly more CLA than the control and the other tocopherol treatments. 1800 ppm γ-tocopherols produced similar CLA levels as 1400 MT (FIG. 4). Thus, the increase in CLA yield in the presence of mixed tocopherols is due to γ-tocopherols. In contrast, α-tocopherol produced similar or less CLA than the control. The larger δ-tocopherols concentrations at 1800 and 1400 ppm, however, produced CLA levels greater than the control but not as high as γ-tocopherols. The lower δ-tocopherol levels reduced CLA content relative to the control.

Figure 8:
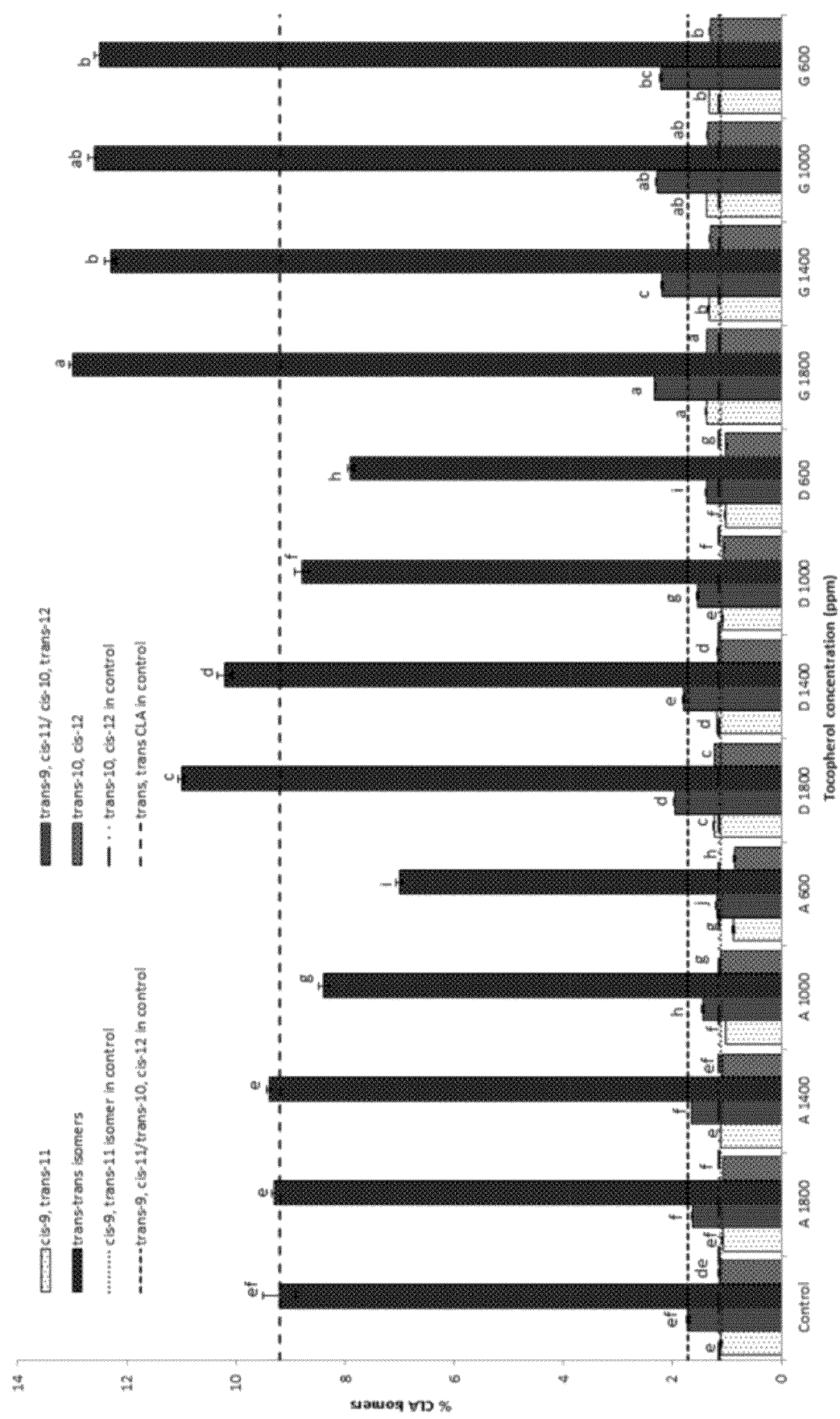
FIG. 8 is a graphical illustration of CLA isomer yields obtained by photo-isomerization of soy oil linoleic acid with oils of various concentrations of α-, γ- and δ-tocopherols, where error bars represent standard error of mean (n≥4) and means with different letters are significantly different at p<0.05.

FIG. 8 illustrates the CLA isomer yields with various tocopherol treatments. The trend in trans,trans CLA is similar to that of total CLA, as shown in FIG. 4 with the minor isomers being present about 1-2% levels. The results appear to demonstrate an increase in minor isomer content with increase in trans,trans CLA.

Figure 9:
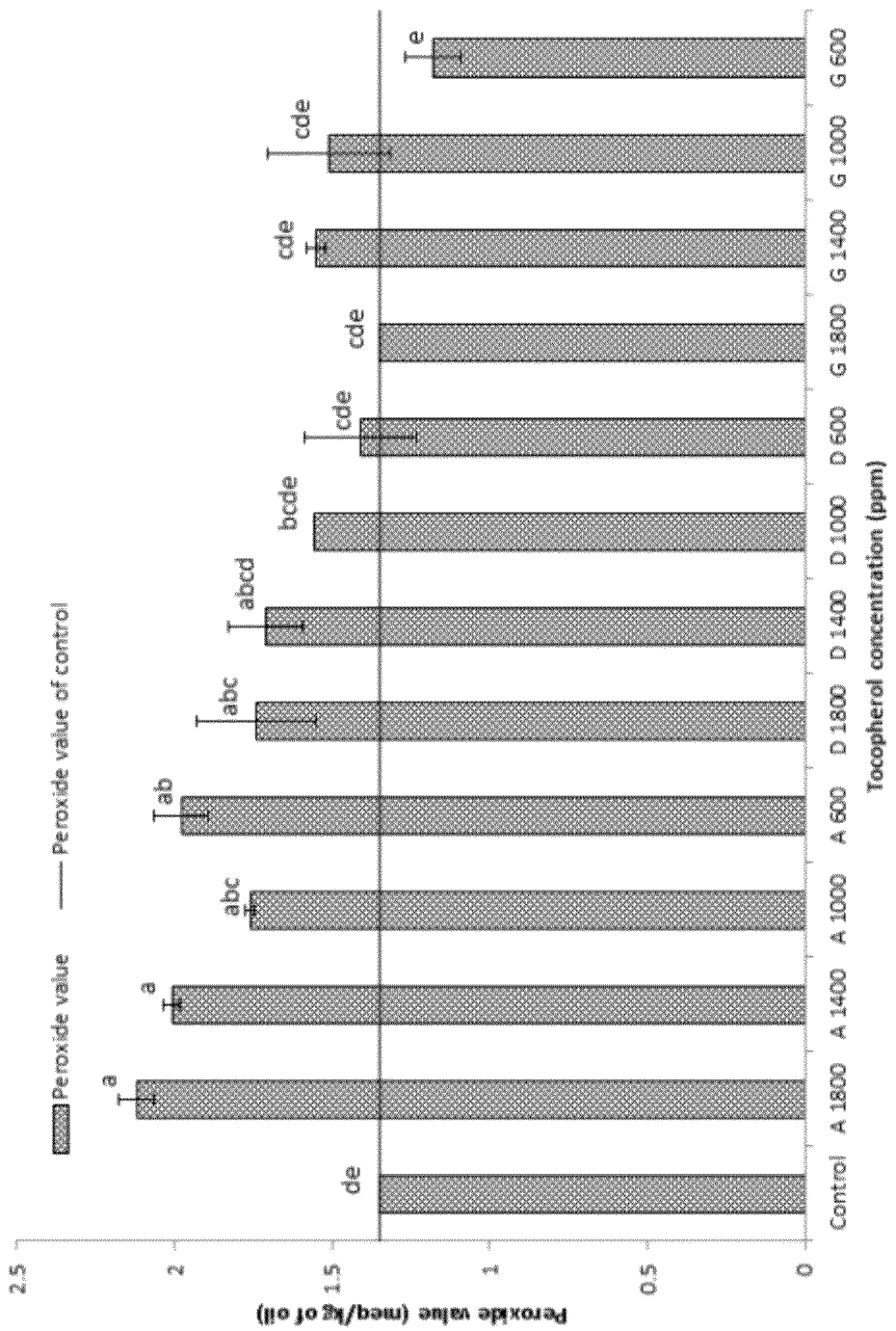
FIG. 9 is a graphical illustration peroxide values of photo-isomerized soy oil with various concentrations of α-, γ- and δ-tocopherols, where error bars represent standard error of means (n≥4) and means with different letters are significantly different at p<0.05.

The effects of various α-, γ- and δ-tocopherols concentrations on soy oil PVs is seen in FIG. 9. The PV of control RBD soy oil without added tocopherols was 1.35 meq/kg of sample. The α-tocopherol treatments produced significantly larger PVs than the control soy oil. The γ- and δ-tocopherols treatments produced PVs similar to the control, except that of the 1800 ppm δ-tocopherol treatment was significantly larger. The antioxidant activity of tocopherols as determined by PV decreased in the order of γ→δ→α-tocopherols. γ-tocopherol produced the most CLA of the tocopherols while α-tocopherol produced the lowest CLA relative to the concentrations of tocopherols investigated. This may be due to the higher stability of γ-tocopherol and faster degradation α-tocopherol of during photoisomerization. Furthermore, the redox potential of α-tocopherol is low when compared to other tocopherols, which implies that it is a stronger hydrogen donor and more vulnerable to oxidation. The depletion periods of tocopherols appears to be related to the period during which they remained effective as antioxidant.

CLA yields increase with increasing antioxidant capacity and antioxidant stability. Soy tocopherols, namely γ-tocopherol, produced more CLA than the synthetic antioxidants treatments at the legal levels of use because they can be used at greater levels. In addition, increase in CLA levels is related to an increase in oxidative stability provided by the antioxidant.

In conclusion, TBHQ, MT and MT with 500 ppm AP γ- and δ-tocopherols within legal limits significantly increase soy oil CLA yields and improve oxidative stability during soy oil photoisomerization.

Example 4

Isolation and Extraction of Soy Oil trans-,trans CLA Fatty Acids

Approximately 5 grams refined, bleached, and deodorized (RBD) soy oil (Wesson; ConAgra, Irvine, Calif.) samples in 7-ml borosilicate glass vials with 0.35% resublimed iodine catalyst (EM science Cheery Hill, N.J., USA) were attached to an illuminated laminar flow photo-irradiation unit with photon flux (power) set to 3.14 mW for 12 hours as described above.

Saponification and acidified was performed to produce free fatty acids for reverse phase gradient HPLC (RP-HPLC) analysis. Ten (10) grams of CLA-rich soy oil was refluxed with 150 mL of 0.5 N potassium hydroxide in methanol at 75° C. with 0.5% butylated hydroxyl toluene (BHT) in a hot water bath for 2 hours. Dilute sulfuric acid was added to decrease the pH to ≤2. The fatty acids were then partitioned into 50 mL of chloroform. The percent fatty acid was determined, and the peroxide value was determined by a micro method. These determinations ensured that detector absorbance was not from lipid diene peroxide oxidation products.

The RP-HPLC was used with two (2) C-18 reversed phase columns in series (Sunfire, Waters Corporation, Milford, Mass.). Two (2) 250 mm×4.6 mm i.d. columns (5 μm particle size) were placed in series, with a 20 mm×4.6 mm i.d guard column. The column temperature was kept at 23° C. using a Temperature Control Module (Waters Corporation, Milford, Mass.).

About 40 μg of the fatty acid mixture in 20 μL chloroform was injected using the Waters 717 plus autosampler and a Waters model 600 gradient system, equipped with a quaternary pump (Waters Delta 600), pumping at rate of 1.0 mL/min. A simple solvent elution linear gradient starting with 85%/15% methanol/water increasing to 100% methanol over 80 min, followed by an isocratic solvent system of 100% methanol (40 min), was used. The retention times of linolenic, linoleic acid, oleic, palmitic and stearic acids and cis, trans CLA was determined by use of fatty acid standards.

The column effluent was connected to a photodiode array (PDA) detector (Waters Model 2996) measuring absorbance at 233 nm. The outlet from the PDA was connected to a Waters Model 2420 evaporative light scattering detector (ELSD) (Waters Corporation, Milford, Mass.) with a drift tube temperature of 50° C., gas pressure of 32 psi, nebulizer temperature at 24° C. and photomultiplier gain at 256. High purity $N_2$ was used as the nebulizer gas. The data output from PDA and ELSD integrated by Waters Empower™ 2 Software (Waters Corporation, Milford, Mass., USA). The CLA fractions, identified by absorbance peaks at 233 nm, were then collected manually for subsequent GC-FID and ATR-FTIR analysis.

The CLA fractions separated by RP-HPLC were converted to FAMEs using a boron trifluoride-methanol complex as the methylating agent for GC-FID analysis. The fatty acid profiles were then analyzed as FAMEs by GC using a SP 2560 fused silica capillary column (100 m×0.25 mm i.d.×0.2 μm film thickness; Supelco Inc., Bellefonte, Pa.) with a flame ionization detector (FID) (model 3800, Varian, Walnut Creek, Calif., USA). The samples were injected by an autosampler (Varian, Walnut Creek, Calif., USA). The sensitivity of the GC instrument was manually maximized using the Galaxie Chromatography Workstation software (version 1.9.3.2) in order to provide sufficient sensitivity. The FID settings were as follows: heater=250° C., sensitivity=12, He gas=30 mL/min, $H_2$=31 mL/min and air=296 mL/min and oven temperature program was 60° C. for 1 minute, then increased at 20° C./min to 170° C./and held this temperature for further 50 min.

CLA fractions were analyzed using an ATR-FTIR spectrum of each oil sample after collection using OMNIC software on an Impact 410 instrument (Nicolet, Madison, Wis.) in the absorption mode. The instrument was equipped with an interferometer with a deuterated triglycine sulfate (DTGS)-KBr detector. The mirror velocity was 0.6329 cm/s and the resolution was 4 $cm^{-1}$. Each sample was subjected to 128 scans, with a data spacing of 1.928 $cm^{-1}$. The background sample was collected using the same instrumental and environmental conditions and was collected every 120 min. The sample holder was cleaned after collection of each sample with methanol/water. Samples were scanned using a wave number range of 1000-900 $cm^{-1}$.

FAMEs were produced from photoisomerized CLA-rich soy oil by base-catalyzed methylation, and silver-ion HPLC separation of trans-,trans-CLA from CLA-rich soy oil was performed. Two (2) ChromSpher 5 Lipids Analytical silver-impregnated columns (each 4.6 mm i.d.×250 mm stainless steel; 5 μm particle size; (Chrompack, Bridgewater, N.J.)) in series were used. The column temperature was kept constant at 23° C. using a Temperature Control Module (Waters Corporation, Milford, Mass.).

About 40 μg CLA-rich oil FAMES in 20 μL hexane was injected was injected using the Waters 717 plus autosampler and a Waters model 600 system, equipped with a quaternary pump (Waters Delta 600), pumping at rate of 1 mL/minute. A simple solvent system having 0.1% acetonitrile (VWR International, West Chester, Pa.) in hexane was used. The column effluent was connected to a photodiode array (PDA) detector (Waters Model 2996, Waters Corporation, Milford, Mass.) measuring absorbance at 233 nm. The data output from PDA was integrated by Waters Empower™ 2 Software (Waters Corporation, Milford, Mass., USA). The CLA fatty acid methyl ester (FAME) fractions separated by silver ion HPLC, identified by absorbance peaks at 233 nm, were then directly injected into GC-FID for further analysis.

The positional isomers were determined in the CLA-rich oil by making CLA derivatives that would enhance MS identification. The study was conducted on CLA-rich oil, rather than trans-,trans-CLA fractions, as there was not sufficient substrate in the trans-,trans-fractions for derivatization. The oil was 15% CLA with 70% of the CLA isomers being trans-, trans- and no other isomer exceeded 3% of the total CLA.

Figure 11:
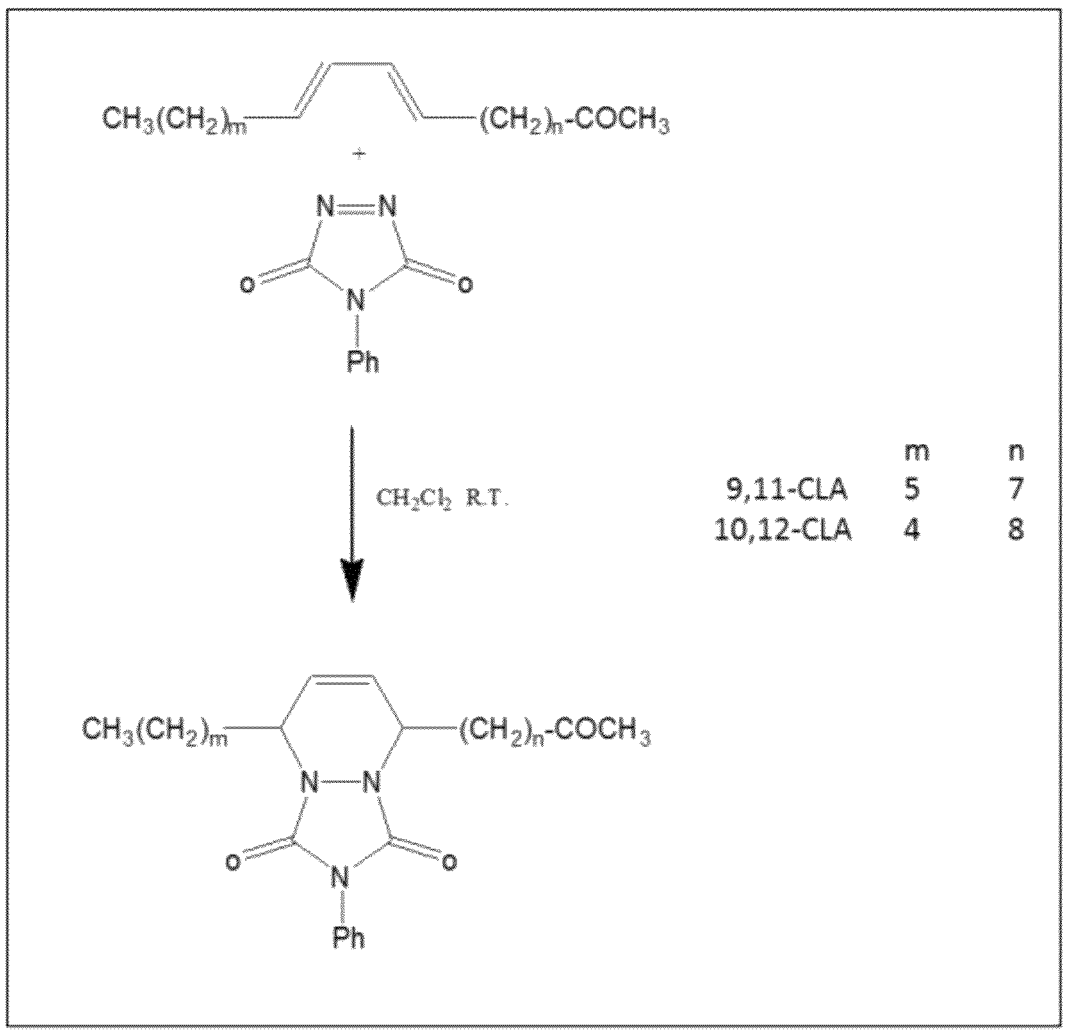
FIG. 11 is a schematic illustration showing reaction of conjugated dienes with 4-Phenyl-1,2,4-triazoline-3,5-dione (PTAD) at room temperature to form Diels Alders CLA-PTAD adduct trapping double bonds in a 6 Member Ring.

CLA-rich oil FAMES were produced, and 4-Phenyl-1,2,4-triazoline-3,5-dione (Sigma-Aldrich, St. Louis, Mo.) adducts of CLA FAMEs were obtained as follows. PTAD (165 mg) of was added to 140 mg of CLA FAMEs in 5 mL methylene chloride and stirred for 20 min to form the Diels Alder CLA adduct as shown in FIG. 11. The excess PTAD was removed by adding the solution to silica-gel column eluting CLA FAMES with 5 mL hexane:ethyl acetate (5:1) solvent. Residual PTAD, being polar, was retained on the column and the relatively non-polar CLA-PTAD adduct eluted. These adduct compounds form unique structures determined by the location of the double bonds. The MS fragmentation patterns are diagnostic for CLA positional isomerism for these adducts. The cyclic structure of these adducts facilitates cleavage at either side of the ring at the specific carbons formerly at the terminal positions of the conjugated diene. Carbon-carbon fragmentation elsewhere within the ring does not produce a fragment having a different mass, as in-ring fragmentation requires breakage of two C—C bonds to produce a change in mass. Cleavage adjacent to the ring is slightly favored compared to within the alkane moiety because production of a secondary rather than a primary carbonium ion is more stable. The ring moiety also enhances the intensity of the molecular ion.

GC-MS analysis of CLA-PTAD adducts was performed using a 20:1 split and Capillary GC-column column ZB-5HT INFERNO (30 m×0.25 mm i.d, 0.25 mm film thickness) was used. The column temperature was programmed at 60° C. to 325° C. at a rate of 10° C./min with 1 min hold at 60° C. and 7 min hold at 325° C.

Figure 12:
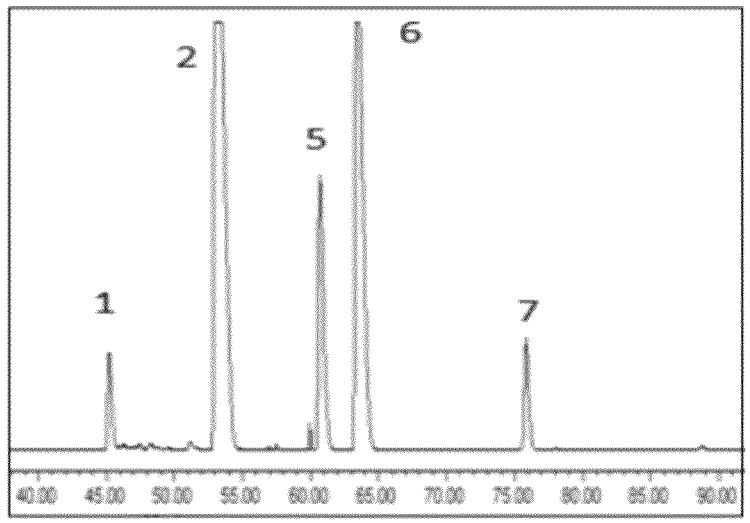
FIG. 12 are chromatograms obtained by ELSD detection of fatty acids in chloroform obtained by saponification and acidification of: A) Control soy oil; and B) CLA-rich soy oil, where fatty acid peaks are: 1=linolenic acid, 2=linoleic acid, 3=CLA isomers, 4=CLA isomers, 5=palmitic acid, 6=oleic acid, and 7=stearic acid, and where soy oil and CLA-rich soy oil samples both contained 86% free fatty acids and had PV of 0.4 and 0.8, respectively.
Figure 12:
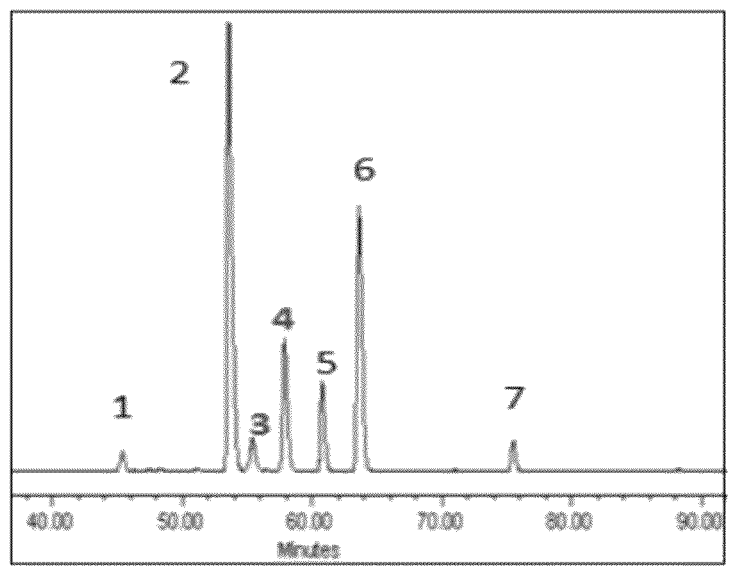

FIG. 12 shows the fatty acid RP-HPLC chromatograms of conventional control soy oil and 15% (±0.6 SD) CLA-rich oil, using an ELSD as a general fatty acid detector. Soy oil and CLA-rich soy oil samples both contained 86% free fatty acids and had PV of 0.4 and 0.8, respectively. The CLA-rich oil fatty acids were composed of the same fatty acids as conventional soy oil, with two additional FAME peaks (3 and 4) in the CLA-rich oil.

Figure 13:
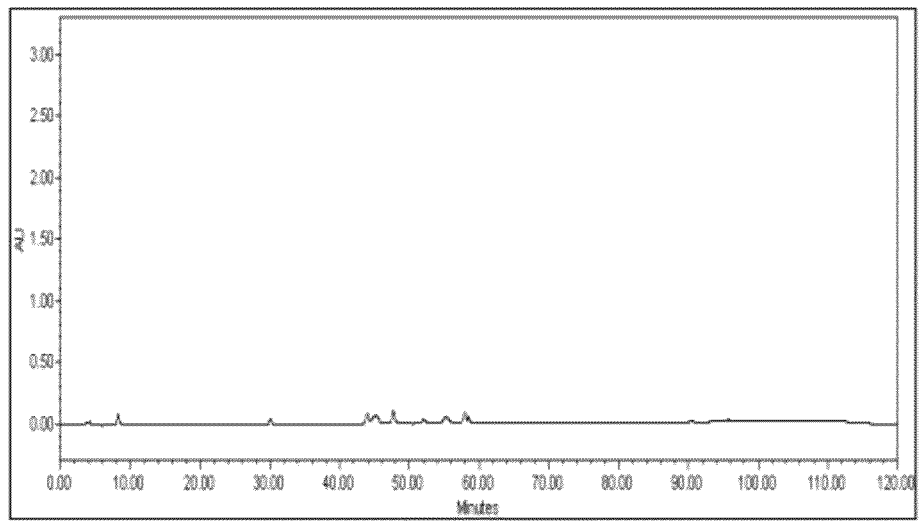
FIG. 13 are chromatograms obtained by absorbance at 233 nm of fatty acids in chloroform obtained by saponification and acidification of: A) Control soy oil; and B) CLA-rich soy oil, where soy oil and CLA-rich soy oil samples both contained 86% free fatty acids and had PV of 0.4 and 0.8, respectively.
Figure 13:
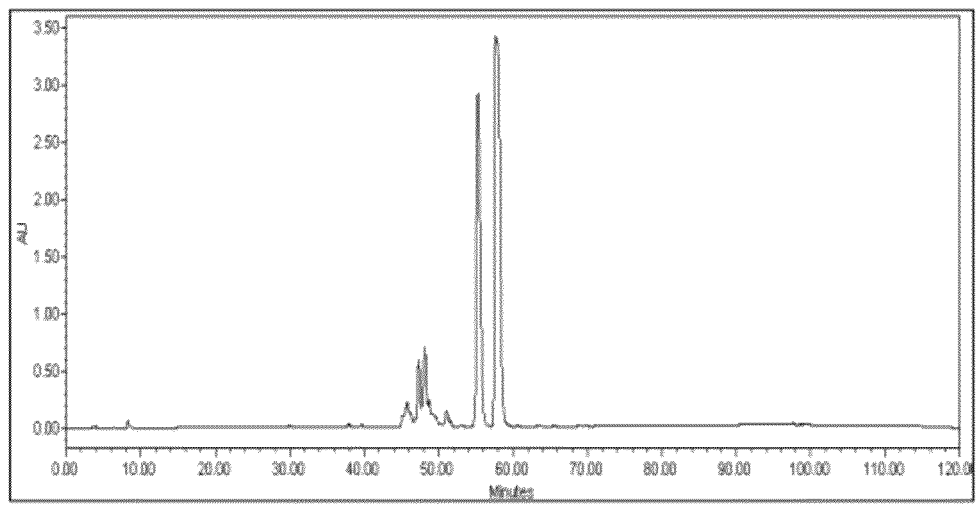

FIG. 13 illustrates the reverse phase HPLC chromatograms of conventional control soy oil and 15% (±0.6 SD) CLA-rich oil with PDA detection at 233 nm. Only a trace of oxidation products is seen in the control, which may be due to the small PV values of 0.4. The CLA-rich oil shows two significant peaks at 54.5 and 57.8 minutes, which are just after the linoleic acid retention time, as shown by ELSD (FIG. 12). It is highly probable that these peaks are CLA isomers, in view of the low PV and that soy oil TAGs containing CLA elute slightly later than the corresponding control soy oil TAGS. A band of much smaller UV absorbing peaks were seen around the retention time of linolenic acid (45 min), suggesting that various conjugated linolenic acid isomers may be also present in CLA-rich oil.

Figure 14:
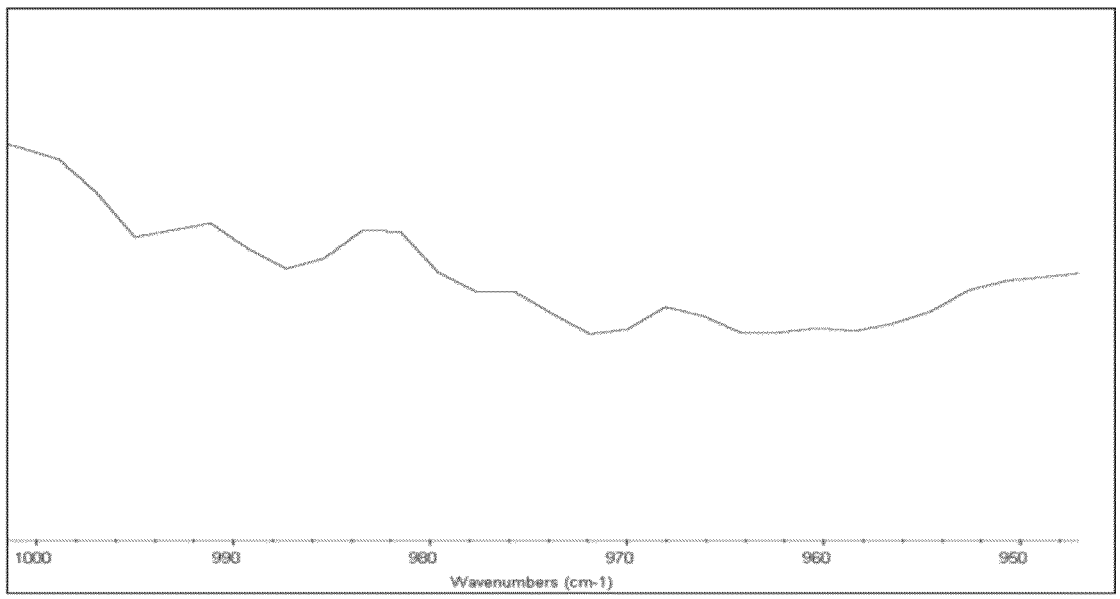
FIG. 14 are ATR-FTIR spectra of fractions 3 and 4, as shown in FIG. 12, obtained by RP-HPLC separation of CLA-rich oil fatty acids.
Figure 14:
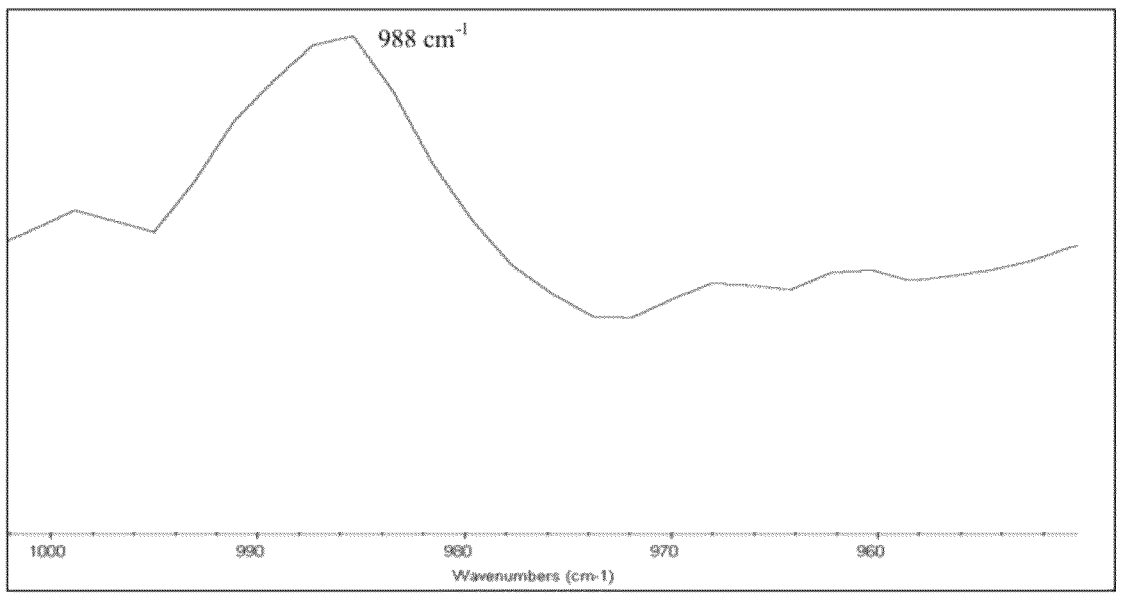

The GC-FID FAME analysis of HPLC peaks 3 and 4 confirmed that peak 3 consisted of 1.78% cis-9,trans-11 CLA; 2.74% trans-9,cis-11 CLA/cis-10,-trans 12 CLA and 1.75% trans-10,cis-12 CLA and that peak 4 was exclusively trans-,trans-CLA isomers. GC-FID FAME analysis performed on HPLC combined peaks 3 and 4 and was found to have the same ratio of CLA isomers as CLA-rich oil. Furthermore, FTIR spectral findings in FIG. 14 confirm the GC-FID results. Peak 3 showed cis,trans and trans, cis absorbance (981 $cm^{-1}$, 947 $cm^{-1}$, respectively) and peak 4 showed only trans,trans absorbance (988 $cm^{-1}$).

Figure 15:
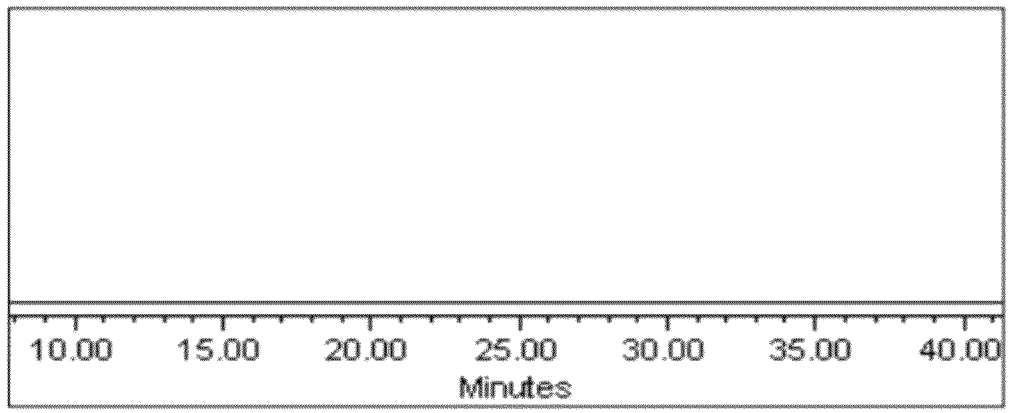
FIG. 15 are chromatograms obtained by UV-PDA detection at 233 nm of: A) Control soy oil; and B) CLA-rich soy oil FAMEs by Silver ion HPLC, where the CLA peaks are assigned according to retention times.
Figure 15:
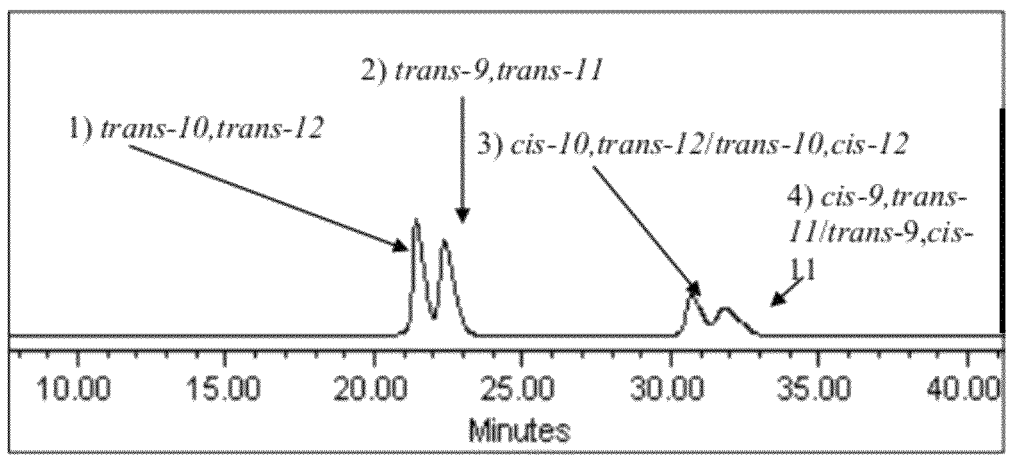
Figure 16:
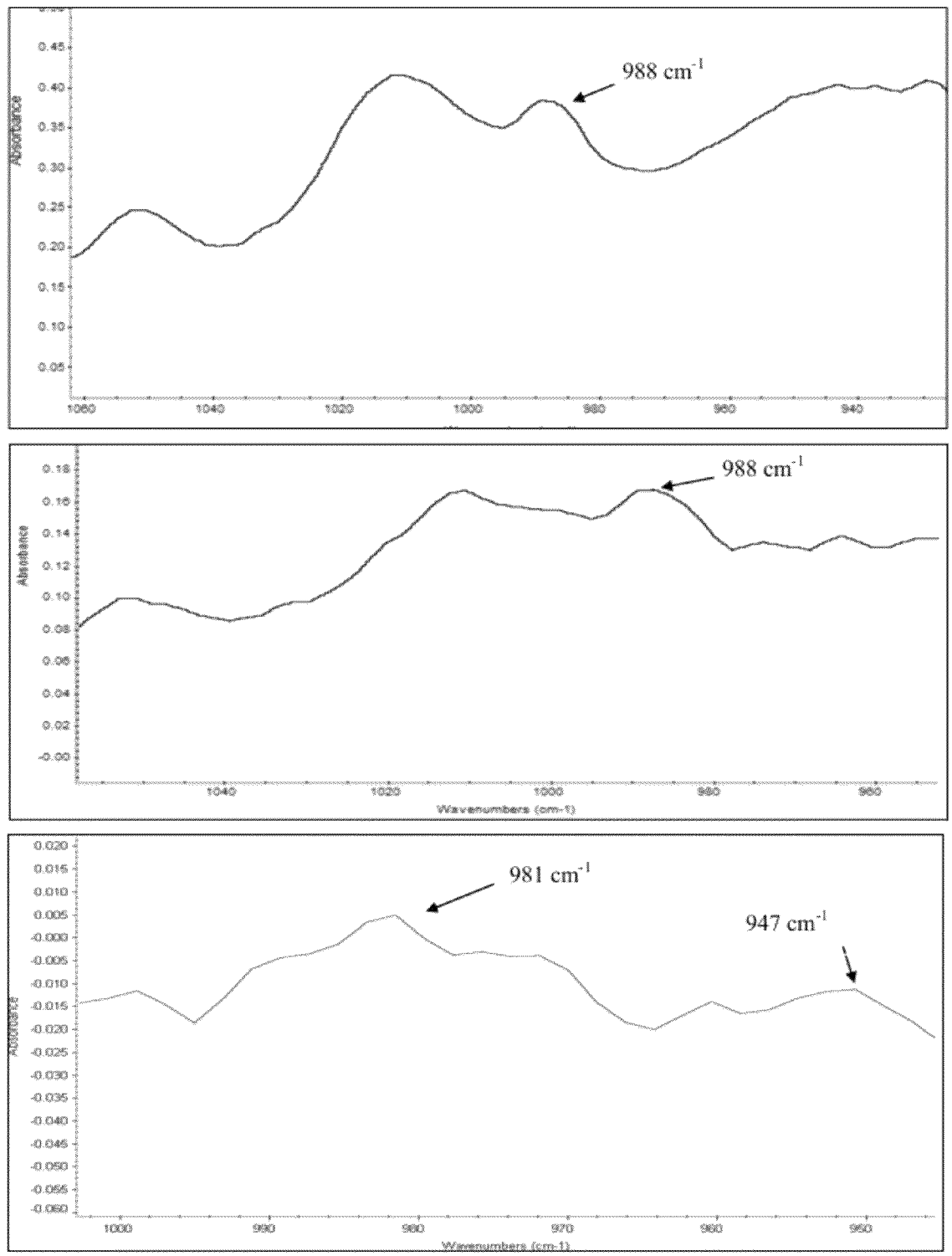
FIG. 16 are ATR-FTIR spectra of fractions obtained by Silver ion HPLC, as shown in FIG. 15, separation of CLA-rich oil FAMEs, where A) fraction 1; B) fraction 2; and C) fractions 3 and 4 combined.

FIG. 15 shows the silver ion chromatogram of CLA-rich soy oil using a PDA detector at 233 nm. The control soy oil FAMES chromatogram did not disturb the baseline as no conjugated compounds were present. The CLA-rich soy oil chromatogram consisted of four peaks distributed as two pairs of peaks. When the retention times were analyzed, the CLA isomers could be assigned as follows: peak 1 is trans-10,trans-12 CLA; peak 2 is trans-9,trans-11 CLA; peak 3 is cis-10,trans-12 and/or trans-10, cis-12 CLA and peak 4 is cis-9,trans-11 and/or trans-9,cis-11 CLA, as labeled in FIG. 15. FAMEs analysis by GC-FID of peaks 1 and 2 was performed to confirm the results for trans, trans CLA. Likewise geometrical isomer analysis by ATR-FTIR was consistent with the trans,trans configuration. Peaks 3 and 4 were combined to have enough substrate for analysis and GC-FID analysis and ATR-FTIR (FIG. 16) confirmed the geometrical isomer assignment.

Figure 17:
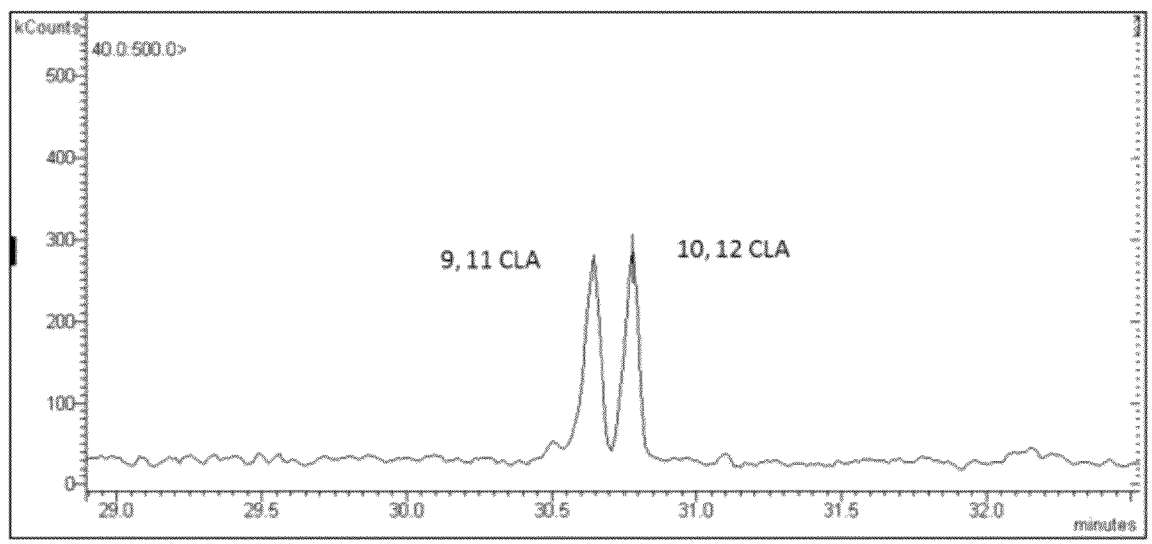
FIG. 17 is total ion chromatogram of products from Diels alder reaction of PTAD with CLA FAMEs from CLA-rich oil purified by silica gel chromatography, where the mass spectra, shown below in FIGS. 19 and 20, of the respective peaks showed that first peak is the PTAD adduct of trans-9,trans-11-CLA while second peak is PTAD adduct of trans-10,trans-12-CLA.
Figure 19:
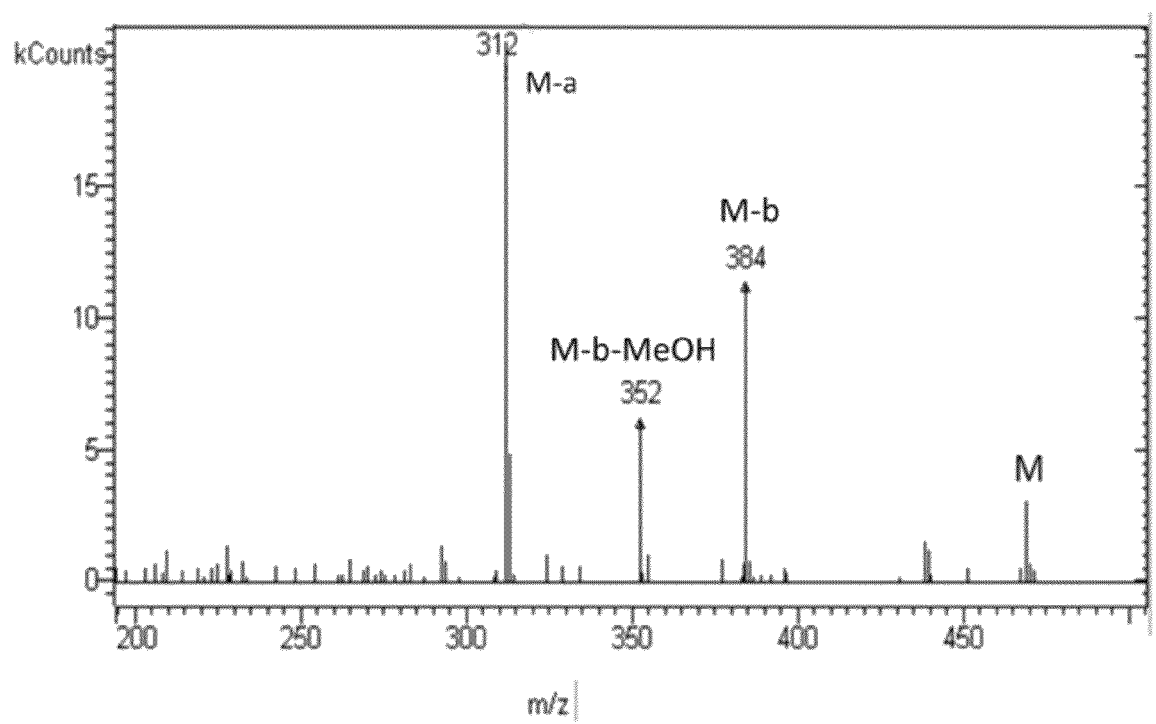
FIG. 19 is mass spectra of first peak of the total ion GC chromatogram, where the fragmentation pattern of the mass spectra shows that first peak is trans-9,trans-11-PTAD-CLA adduct.
Figure 20:
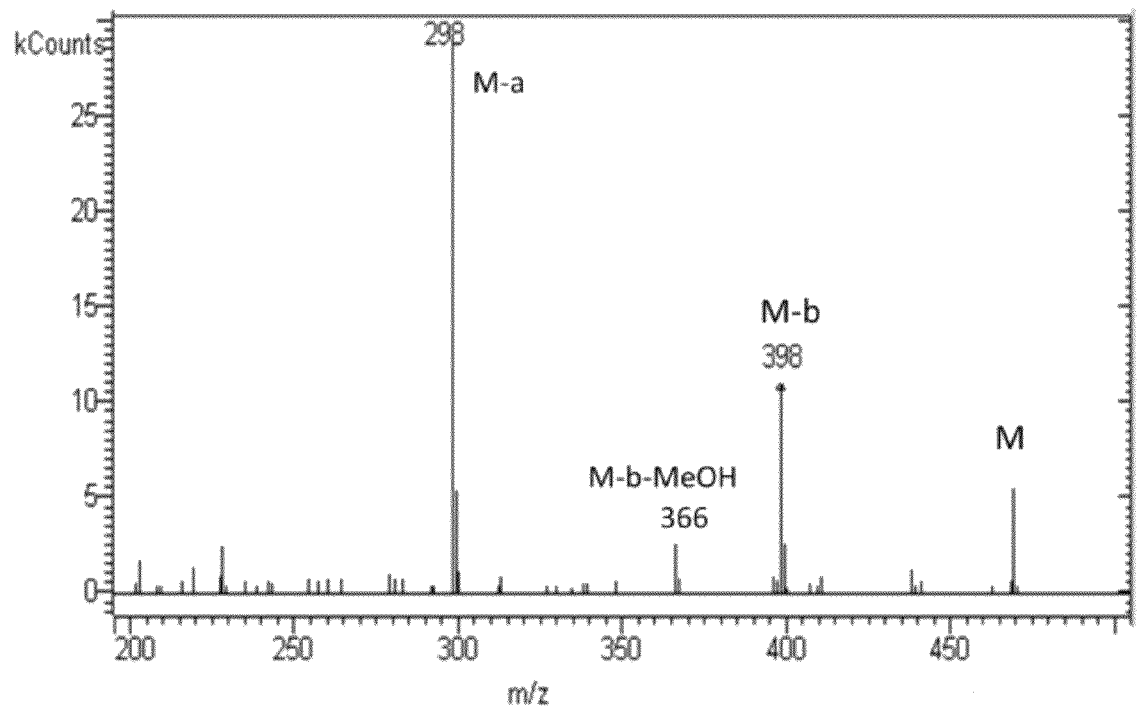
FIG. 20 shows the mass spectra of second peak of the total ion GC chromatogram, where the fragmentation pattern of the mass spectra shows that second peak is trans-10,trans-12-PTAD-CLA adduct.

FIG. 17 shows the total ion chromatogram of products from the Diels Alder reaction of PTAD with CLA FAMEs from CLA-rich oil. Two peaks eluted very close to each other with retention times of 30.64 min and 30.77 min. The mass spectra of the respective peaks are shown in FIGS. 19 and 20. The fragmentation scheme of derivatised CLA is shown in FIG. 8. These data indicate that first peak is the trans-9,trans-11-CLA adduct while the second is trans-10,trans-12-CLA adduct.

Figure 18:
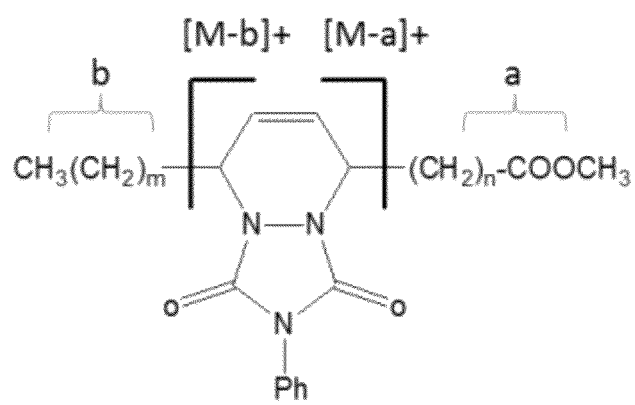
FIG. 18 is a schematic illustrating fragmentation of trans-9,trans-11-CLA and trans-10,trans-12-CLA after derivatization in accordance with an illustrative embodiment of the trans-,trans-conjugated linoleic acid compositions and use thereof disclosed herein.

FIG. 19 shows the mass spectra of first peak of the total ion GC chromatogram. The ion at 469 was identified as the molecular ion. The ring structure enhances the relative abundance of this ion based on comparison to archival spectra from the parent FAMEs of similar dienes. Cleavage occurs on either side of the six-membered ring indicating location of the carbons that originally constituted the conjugated double bond system. For PTAD derivative of trans-9,trans-11-CLA isomer, the position of the nitrogen containing ring between carbon 9 and 12 of the hydrocarbon chain is indicated by alpha-cleavage to the ring to give m/z=384 and 312. Loss of methanol from the ion containing the carboxyl moiety (with m/z 384) at m/z=352 is also consistent with the structure as shown in FIG. 18.

The mass spectrum of second peak of the total ion GC chromatogram was similar (FIG. 20). Again the intense 469 was identified as a strong molecular ion peak. For a PTAD derivative of the trans-10,trans-12-CLA isomer, the position of the nitrogen containing ring formed by a Diels Alder reaction with a diene between carbon 10 and 13 is indicated by alpha-cleavage to give ions a m/z=298 and 398. Again, loss of methanol from the ion containing the carboxyl moiety (with m/z 398) gives an additional fragment a m/z=366.

The HPLC, IR and MS studies show that CLA-rich oil trans-,trans-CLA isomers are 9,11 and 10,12. There may be slightly more of the trans-10,trans-12-CLA isomers formed as shown by the relative peak height in the silver ion HPLC data (FIG. 15) and GC-MS chromatogram (FIG. 17). Furthermore, the MS and silver-ion chromatography data symbiotically show that the cis-,trans- and trans-,cis-isomers also have this positional isomerism (9,11 and 10,12). In addition, the chromatographic conditions for separation of trans-,trans-fatty acids from other CLA-rich FAMEs have been determined and the means to separate trans-,trans-CLA isomers.

Kinetic data has shown that trans-,trans-CLA is rapidly formed from other CLA isomers, and a free radical mechanism rationalizing the formation of the various CLA isomers is shown in FIG. 10. High intensity UV-radiation cleaves $I_2$ homologously and I., thus formed abstracts H-atom from C-11 of Linoleic acid to form a radical. As the lipid radical is unstable, resonance stabilization occurs forming a more stable CLA radical intermediate. H-atom from HI binds with C-13 of CLA radical intermediate. Then, an H-atom from HI binds with C-9 of CLA radical intermediate and I. and I. form $I_2$. The product then obtained is trans-10,cis-12 CLA or trans-9,cis-11 CLA. In a second reaction, I. adds to C-12 of trans-10,cis-12 CLA creating σ bond and a trans product. Addition of I. allows free rotation around C-12 of iodoalkene radical intermediate. I. abstracts I. from iodoalkene radical intermediate to give the product: trans-10,trans-12-CLA. Similarly, trans-9,trans-11-CLA isomers can also be formed depending on the resonance stabilization configuration the linoleic acid radical adopts.

Example 5

Effect of Trans-Trans Conjugated Linoleic Acid Enriched Soybean Oil on Fatty Liver and Cholesterol in Zucker Rats Thirty-six (36) 3-month old female Zucker rats (Harlan Laboratories, Indianapolis, Ind.) were divided into the following twelve (12) treatment groups: lean control (L-Ctrl), obese control (O-Ctrl), and obese CLA (O-CLA). The L-Ctrl and O-Ctrl groups were fed AIN-93M purified rodent diet. The O-CLA group was fed AIN-93M modified to contain about 0.5% trans-,trans-CLA isomers by diet mass. All animals were pair-fed to the mean intake of the L-Ctrl group and the food intake was measured three times a week. Although pair-feeding may cause stress in hyperphagic obese Zucker rats, no visual signs of stress was observed. Pair-feeding was necessary to match the macronutrient intake of all the groups. The body weight of the animals was recorded once per week. The rats had free access to deionized water. After 100 days of treatment, the rats were fasted for 12 h before being sacrificed by exsanguination via cardiac puncture.

Animals in the control group were fed AIN-93M purified rodent diet formulated in accordance to the American Institute of Nutrition committee report. Animals in the O-CLA group received AIN-93M containing 40 g/kg of trans-,trans-CLA-rich soy oil substituted for regular soybean oil.

TABLE 6

Rat Diet Composition

| Ingredients[a] (g/1000 g) | Ctrl[b] | CLA[c] |
|---|---|---|
| Cornstarch | 435.692 | 435.692 |
| Maltodextrin | 155 | 155 |
| Sucrose | 100 | 100 |
| Casein | 170 | 170 |
| Soybean oil | 40 | 0 |
| t,t-CLA-rich soy oil[d] | 0 | 40 |
| Cellulose | 50 | 50 |
| AIN-93-VX vitamin mix | 10 | 10 |
| AIN-93M-MX mineral mix | 35 | 35 |
| TBHQ[e] | 0.008 | 0.008 |
| L-Cysteine | 1.8 | 1.8 |
| Choline bitartrate | 2.5 | 2.5 |

[a]Diet ingredients were purchased from Harlan (Harlan Laboratories, Indianapolis, IN) unless otherwise noted.
[b]Ctrl = Control Diet
[c]CLA = CLA diet
[d]Produced by photoisomerization of soy oil.
[e]ACROS Organics (New Jersey, USA)

RBD soy oil was photo-irradiated using the photo-irradiation system. The total CLA and isomer content of the oil was measured as FAMEs by base-catalyzed conversion. The CLA isomer composition of the CLA-rich soybean oil is presented below in Table 7.

TABLE 7

Isomeric Composition Of Soybean Oil Used In Experimental Diet

| CLA Isomer | Average concentration (%) |
|---|---|
| c9, t11 CLA | 1.25 |
| t9, c11/c10, t12 CLA | 2.26 |
| t10, c12 CLA | 1.19 |
| t, t[a] CLA | 13.73 |
| Total CLA | 18.43 |

[a]Consists of trans-8, trans-10 CLA, trans-9, trans-11 CLA, and trans-10, trans-12 CLA Dual-Energy X-ray Absorptiometry (DXA; GE Lunar DXA, Waukesha, Wis.) was used to analyze the body composition of the rats at baseline and immediately prior to sacrifice. The animals were anesthetized and placed stomach down on the scan bed of the DXA. The absorbance of two (2) X-ray beams was measured and percent lean tissue and percent fat tissue were calculated by software (enCORE, GE Lunar, Waukesha, Wis.) appropriate for the body composition assessment of small animals.

Organs and tissues of interest were removed from the animal immediately after sacrifice. The heart, liver, and white adipose tissue were placed in cryogenic storage containers and flash-frozen in liquid nitrogen before being stored at $-80°$ C. Approximately 7 mL of blood collected from the animal via cardiac puncture during sacrifice was stored on ice before being centrifuged to separate serum from whole blood. Aliquots of serum were transferred to microcentrifuge tubes and stored at $-80°$ C. until analysis. A small amount of blood collected from the heart during sacrifice was placed in a microtube containing $K_2$ EDTA (an anticoagulant) and stored at $-80°$ C.

Serum triglycerides (TG), total cholesterol (TC), high density lipoprotein-cholesterol (HDL-C), low density lipoprotein-cholesterol (LDL-C), aspartate transaminase (AST), blood urea nitrogen (BUN), glycated hemoglobin (HbA1c), and glucose concentrations were determined using commercially available kits from Alfa Wassermann Diagnostic Technologies (West Caldwell, N.J.). An ACE Alera clinical chemistry system (Alfa Wassermann Diagnostic Technologies, West Caldwell, N.J.) was used according to the manufacturer's instructions to perform these tests.

Serum insulin was quantified using a commercially available ELISA kit (Alpco Immunoassays, Salem, N.H.). An aliquot of serum was thawed at 2-8° C. before use. A 96-well plate in the kit was prepared per manufacturer instructions to include duplicate standards, appropriate controls, and sample duplicates. Absorbance was measured using a BioTek ELx808 microplate reader (Winooski, Vt.) attached to a PC running BioTek Gen5 data analysis software (Winooski, Vt.).

One (1) gram of liver was homogenized in a 20-fold volume of 2:1 chloroform-methanol (v/v) mixture. Following homogenization, 0.58% NaCl solution was added to achieve separation of the phases and centrifuged for 20 min at 500×g. Supernatant was discarded and the organic phase was filtered and washed with chloroform through fat free filter paper (3.2 cm Whatman, Whatman International Ltd, Maidstone, England). The filtered organic phase containing the tissue lipids was then transferred to a pre-weighed scintillation vial. Liver lipids and total cholesterol were determined.

RNA was extracted from approximately 100 mg of white adipose tissue by Trizol Reagent using RNeasy Lipid Tissue Mini Kit (Qiagen, USA), and total RNA from rat heart was extracted using Trizol (Invitrogen, Carlsbad, Calif.). Rat heart tissues were homogenized in ground glass homogenizer using Trizol (1 mL/100 mg tissue) and were transferred to 1.5 mL microcentrifuge tube. The final washed pellets of RNA were dissolved in 40 µl of RNase free water. The total amount of RNA present in each sample was quantitated using Nanodrop (Thermo Scientific, Wilmington, Del.) and 1 µg/sample of total RNA was used for cDNA synthesis using Bio-Rad iSCRIPT cDNA synthesis kit (Bio-Rad, Hercules, Calif.).

Following cDNA synthesis, real-time qPCR was performed using the Bio-Rad iQ with SYBERGREEN PCR system (Bio-Rad, Hercules, Calif.). Real-time PCR primers were designed using Primer3 primer design software and all primer sets were synthesized by Invitrogen (Invitrogen, Carlsbad, Calif.). Primer sequences used for this study are summarized in Table 8. The real-Time PCR was performed on the Bio-Rad iCYCLER real-time PCR instrument (Bio-Rad, Hercules, Calif.). The following experimental conditions were used for all target gene expression including generation of standard curves. The initial denaturation cycle was performed at 95° C. for 5 min. All subsequent denaturation and annealing cycles were repeated 45 times at 95° C. for 15 s and 60° C. (55° C. annealing for reference gene β-actin) for 45 s, respectively. The relative gene expression ratio by real-time qPCR was calculated using "REST" software.

TABLE 8

Primers Used In Real Time Qper

| Gene name | Gene bank accession no. | | Primer sequence | BP size |
|---|---|---|---|---|
| β-Actin | BC138614 | Forward | AGATCTGGCACCACACCTTC | 139 |
| | | Reverse | GGGGTGTTGAAGGTCTCAAA | |
| PPAR-γ | NM_013124 | Forward | GACCACTCCCATTCCTTTGA | 109 |
| | | Reverse | CAACCATTGGGTCAGCTCTT | |

The data analysis involved estimation of means and Standard Error (SE) using JMP 8 (2009 SAS Institute Inc. Cary, N.C.). The effects of treatment were analyzed by one-way ANOVA model followed by post hoc analysis using the Fisher's least squares means separation test when F values were significant. For all analyses, a P-value less than 0.05 was considered significant.

There were no significant differences (P<0.05) in the mean food intake between the three experimental groups, as the rats were pair-fed to the mean intake of the L-Ctrl group. The effects of treatment on body weights, body composition, and organ weights are shown in Table 9. There were no significant differences in the final body weights or body composition of O-Ctrl and O-CLA groups. A significant difference was found between the body weights and body composition of the L-Ctrl group when compared to the O-Ctrl and O-CLA group. The liver weights of the O-CLA group were significantly lower than those of the O-Ctrl, but were significantly higher than the liver weights for the L-Ctrl group (P<0.05). These results provide evidence that trans-,trans-CLA enriched soy oil reduces organomegaly in fa/fa obese Zucker rats.

TABLE 9

Effects of CLA Enriched Soybean Oil on Food Consumption, Body Weight, Body Composition, and Organ Weights in Obese Zucker Rats

| | L-Ctrl | | O-Ctrl | | O-CLA | |
|---|---|---|---|---|---|---|
| | Mean | SE | Mean | SE | Mean | SE |
| Average food consumption (g/day) | 17.0 | 2.4 | 18.00 | 1.4 | 18.1 | 1.4 |
| Initial body weight (g) | $179.2^b$ | 4.1 | $329.9^a$ | 9.4 | $330.3^a$ | 6.7 |
| Final body weight (g) | $300^b$ | 6.6 | $551.9^a$ | 9.4 | $538.4^a$ | 6.9 |
| Initial body fat % | $24^b$ | 2 | $81^a$ | 2 | $81^a$ | 2 |
| Final body fat % | $36^b$ | 3 | $82^a$ | 2 | $85^a$ | 2 |
| Liver weight (g) | $8.57^c$ | 0.61 | $31.34^a$ | 1.81 | $20.48^b$ | 1.75 |
| Liver weight (g/100 g bwt) | $2.83^c$ | 0.13 | $5.8^a$ | 0.29 | $3.73^b$ | 0.34 |

Data represents the mean values and standard error (SE; n = 12/group). Values in a row without common superscripts are significantly different (P < 0.05).

The serum lipid profiles are presented in Table 10. The serum TC and LDL-C concentrations of the rats in the O-CLA group were significantly lower compared to the control, 41% and 50%, respectively. There was no difference in the TG and HDL-C levels in rats in the O-CLA and O-Ctrl group. This indicates that CLA was able to reduce the total cholesterol concentration without lowering the HDL-C. All serum lipid parameters measured (TC, LDL-C, HDL-C, and TG) were significantly lower in the L-Ctrl group when compared to the O-CLA and O-Ctrl groups (P<0.05).

TABLE 10

Effects of CLA Enriched Soybean Oil on Serum and Liver Lipids in Obese Zucker Rats

| | L-Ctrl | | O-Ctrl | | O-CLA | |
|---|---|---|---|---|---|---|
| | Mean | SE | Mean | SE | Mean | SE |
| Cholesterol (mmol/l) | $2.16^c$ | 0.09 | $13.32^a$ | 1.53 | $7.86^b$ | 1.14 |
| HDL-C (mmol/l) | $0.58^b$ | 0.02 | $1.8^a$ | 0.1 | $1.7^a$ | 0.17 |
| LDL-C (mmol/l) | $0.13^c$ | 0.01 | $1.39^a$ | 0.18 | $0.7^b$ | 0.15 |
| Triglycerides (mmol/l) | $0.97^b$ | 0.09 | $1.95^a$ | 0.31 | $1.87^a$ | 0.23 |
| Liver lipid % | $9.7^c$ | 0.4 | $32.9^a$ | 1.3 | $20.1^b$ | 1.8 |
| Liver cholesterol % | $21.9^b$ | 0.4 | $23.7^a$ | 0.3 | $23.4^a$ | 0.6 |

Data represents the mean values and standard error (SE; n = 12/group). Values in a row without common superscripts are significantly different (P < 0.05). Cholesterol, HDL-C, LDL-C, and triglycerides were measured in serum. Liver lipid percentage and liver cholesterol percentage were measured in the liver. Liver lipid percentage refers to the percentage of total liver weight found to be lipid. Liver cholesterol percentage refers to the percentage of liver lipids found to be cholesterol.

The liver lipid data is also presented above in Table 10. Percent total liver lipids were significantly different among the experimental groups. Percent liver lipids in the O-CLA group were significantly lower than the percent liver lipids in the O-Ctrl group. The reduced liver lipid content of the O-CLA group could explain the lower liver weights in the O-CLA group compared to the O-Ctrl group, and also supports trans-,trans-CLA-rich soy oil supplementation lowers the accumulation of fat in the liver. The percentage of liver cholesterol was reported as the ratio of cholesterol to total liver lipids. No significant differences were found between the percent liver cholesterol in rats in the O-CLA and O-Ctrl group, and rats in the L-Ctrl group showed significantly (P<0.05) lower liver cholesterol values than the O-Ctrl and O-CLA groups.

The serum and whole blood metabolite results are presented in Table 8. Glucose and AST levels in the L-Ctrl group were significantly lower than in the O-Ctrl and O-CLA groups. There was no significant difference in the AST level between the O-CLA and O-Ctrl group. Rats in the L-Ctrl group also had serum insulin values significantly lower than the O-Ctrl group. CLA supplementation had an intermediary effect in lowering the serum insulin levels as the values were not different from either L-Ctrl or O-Ctrl groups. The HbA1c levels of the rats in the O-CLA treatment were found to be significantly lower than the O-Ctrl group, indicating that CLA supplementation effectively regulates the blood sugar levels.

TABLE 8

Effects of CLA Enriched Soybean Oil on Serum and Whole Blood Parameters in Obese Zucker Rats

|  | L-Ctrl | | O-Ctrl | | O-CLA | |
| --- | --- | --- | --- | --- | --- | --- |
|  | Mean | SE | Mean | SE | Mean | SE |
| Aspartate transaminase (g/l) | 9.58[b] | 0.5 | 30.8[a] | 3.4 | 23.4[a] | 4.5 |
| Total protein (g/l) | 0.79 | 0.02 | 0.76 | 0.03 | 0.72 | 0.04 |
| Blood urea nitrogen (mmol/l) | 5.95 | 0.45 | 5 | 0.21 | 5.71 | 0.45 |
| Glucose (mmol/l) | 14.1[b] | 0.6 | 26.1[a] | 1.5 | 27.9[a] | 1.4 |
| Insulin (μg/l) | 0.22[b] | 0.03 | 2.11[a] | 0.68 | 1.25[ab] | 0.16 |
| % HbA1c | 3.51[c] | 0.06 | 3.89[a] | 0.07 | 3.71[b] | 0.05 |

Data represents the mean values and standard error (SE; n = 12/group). Values in a row without common superscripts are significantly different (P < 0.05).

Figure 21:
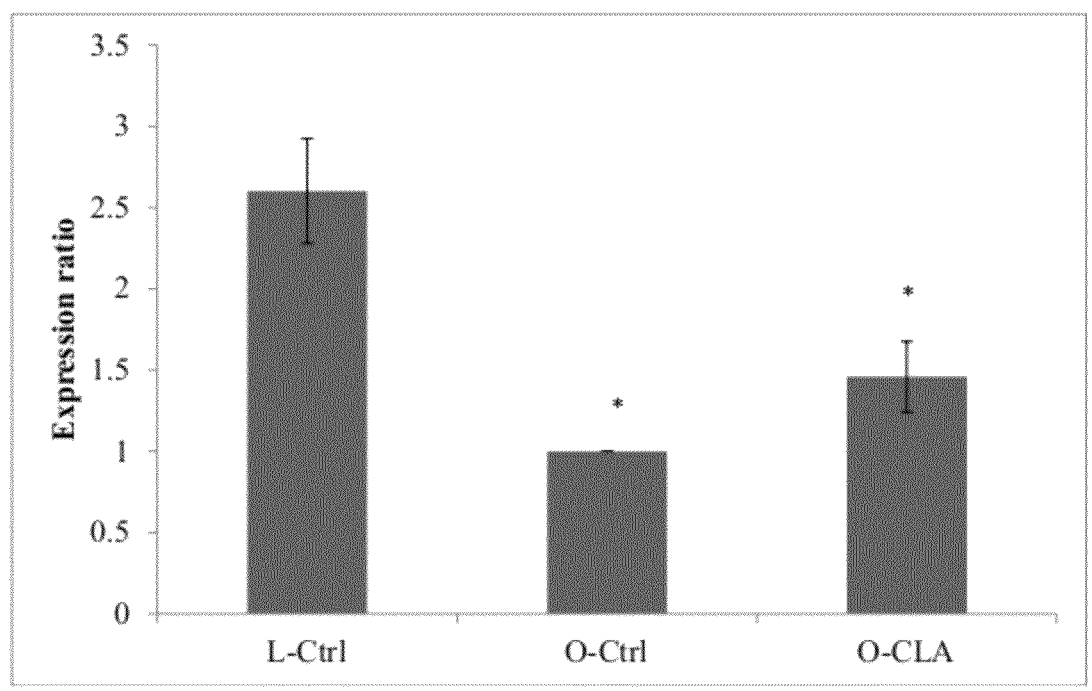
FIG. 21 is a graphical illustration of expression of PPAR-γ in Zucker rat adipose tissue treated with trans-,trans-CLA compared to obese control by RT-PCR, where β-actin was an internal control, results are expressed as a percentage ratio of the control value, values are means, standard errors represented by vertical bars (n=4), and * represents significant difference (P<0.05) compared to the lean control.

The expression of PPAR-γ in white adipose tissue (WAT) was also measured, and no significant difference in the expression of PPAR-γ in the O-CLA group when compared to the O-Ctrl group was found (FIG. 21). The expression of PPAR-γ mRNA in both O-Ctrl and O-CLA groups were significantly lower than the L-Ctrl group.

Figure 22:
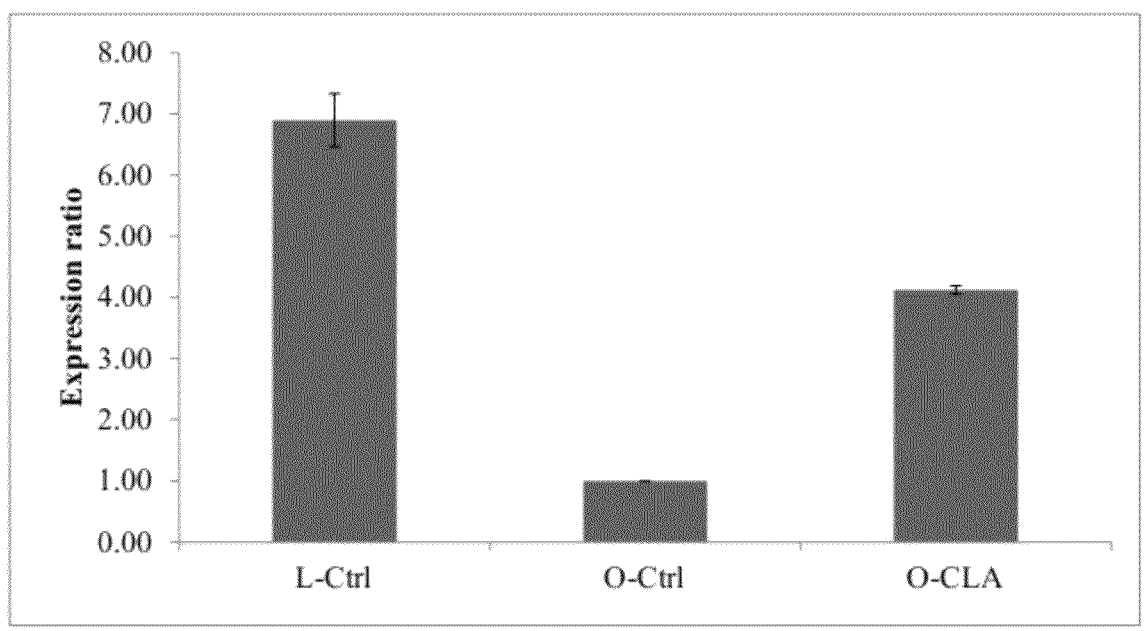
FIG. 22 is a graphical illustration of expression of PPAR-γ in Zucker rat hearts treated with trans-,trans-CLA compared to obese control by RT-PCR, where β-actin was an internal control, results are expressed as a percentage ratio of the control value, values are means, standard errors represented by vertical bars (n=4), and * represents significant difference (P<0.05) compared to the lean control.

The results for relative gene expression of PPAR-γ in heart are presented in FIG. 22. PPAR-γ is a class of nuclear receptors associated with cardiovascular diseases. The gene expression of PPAR-γ in the heart tissue of obese rats was measured, and the results show that dietary supplementation of trans-,trans-CLA enriched soybean oil resulted in significant (P<0.05) upregulation of PPAR-γ in the heart tissue when compared to the O-Ctrl group.

As demonstrated, trans-,trans-CLA-rich soy oil has no effect on the body composition Nonetheless, the trans-,trans-CLA isomers are effective in reducing hepatic steatosis, and trans-,trans-CLA-rich soybean oil can prevent organomegaly by reducing lipid accumulation in the liver. Excess accumulation of lipid in the liver is associated with insulin resistance, and dietary supplementation of trans-,trans-CLA lowered the HbA1c, a long-term measure of glucose control and reduced the circulating insulin levels, moderately but not significantly, in the obese rats. Further, no effects on fasting glucose levels were observed, since the insulin-sensitizing effect of CLA is believed to be by activation of peroxisome proliferator-activated receptor-γ (PPAR-γ). Polyunsaturated fatty acids and their metabolites have been identified as PPAR-γ ligands, and therefore, insulin sensitizing effects of trans-,trans-CLA-rich soy oil may be due to prevention of hepatic steatosis and moderate upregulation of PPAR-γ.

Trans-,trans-CLA-rich soybean oil supplementation in obese rats also reduced the serum cholesterol and LDL-C levels. This decreased serum cholesterol and LDL levels by CLA rich soybean oil can be due to a possible transcriptional activation of the LDL receptor gene which in turn enhances the uptake of VLDL and LDL cholesterol via hepatic LDL receptors. Other possible cholesterol lowering effects of CLA could be due to inhibition of secretion of apolipoprotein B or by inhibiting cholesterol absorption by down-regulating the intestinal sterol O-acyltransferase activity.

Dietary supplementation of CLA rich soybean oil significantly (P<0.05) reduced the total liver lipid content. The lack of significant difference in the AST, BUN, or total protein, supports the finding that liver function was not adversely affected by CLA supplementation. Increased fatty acid oxidation is associated with reduced LDL secretion rate, and lower serum LDL levels in the obese rats supplemented with trans-trans CLA were observed. In addition, hepatic fatty acid synthesis may be strongly downregulated by trans-,trans-CLA. CLA typically enhances the mRNA levels of lipogenic enzymes and their activity with concomitant reduction in the body fat content; however, the trans-trans isomer in CLA enriched soy oil did not lower the body fat percentage, which further supports trans-,trans-CLA preventing hepatomegaly, lowering the hepatic lipid content and improving the serum lipid profiles by increasing the hepatic fatty acid oxidation rather than compensatory increase in the hepatic lipogenesis.

Finally, trans-,trans-CLA induced the mRNA expression of PPAR-γ in the heart tissue of the obese rats. Although originally found to be critical in adipogenesis and regulating insulin signaling, PPAR-γ is also important in the cardiovascular system. Trans-,trans-CLA significantly upregulates the expression of PPAR-γ in obese rat hearts. PPAR-γ agonists can lower blood pressure and inhibit the hypertrophy of cardiomyocytes induced by the mechanical stress. In addition, PPAR-γ activation prevents atherosclerosis by anti-inflammatory activity and its role in modulating lipid homeostasis in macrophages. PPAR-γ inhibits inflammation by binding to NF-κB and facilitating its nuclear export in intestinal Caco-2 cells. Activation of NF-κB transcription factor plays an important role in the hypertrophic growth of the myocardium, which can lead to heart failure. Elevated activity of NF-κB has been reported in cardiomyocyte-specific PPAR-γ knock out mouse hearts. PPAR-γ deficiency-induced NF-κB activation is a likely mechanism in cardiomyocyte-induced cardiac hypertrophy.

In summary, dietary supplementation with soy oil rich in trans-,trans-CLA isomers is effective in improving blood lipids profiles. Trans-,trans-CLA-rich soy oil supplementation also effective in lowering liver lipid content and glycated hemoglobin values, indicating that trans-,trans-CLA can be utilized in regulating blood sugar.

Whereas, the compositions and methods have been described in relation to the drawings and claims, it should be understood that other and further modifications, apart from those shown or suggested herein, may be made within the spirit and scope of this invention.

What is claimed is:

1. A method for enriching soy oil with conjugated linoleic acid, said method comprising the steps of:
   a. admixing said oil with a catalytic amount of iodine in the presence of at least 1,400 ppm tocopherol to form an oil-catalyst admixture;
   b. photoirradiating said oil-catalyst admixture to produce a trans-9, trans-11- and trans-10,trans-12-conjugated linoleic acid-rich soy oil; and
   c. extracting said iodine from said conjugated linoleic acid-rich soy oil.

2. The method of claim 1 wherein said tocopherol is γ-tocopherol.

3. The method of claim 2 wherein said at least 1,400 ppm γ-tocopherol is approximately 1,400 ppm to approximately 1,800 ppm γ-tocopherol.

4. The method of claim 1 wherein said conjugated linoleic acid-rich soy oil contains approximately 75% trans-9,trans-11- and trans-10,trans-12 positional isomers of conjugated linoleic acid.

5. The method of claim 1 wherein said step of extracting said iodine from said conjugated linoleic acid-rich soy oil uses ultrafiltration, and said ultrafiltration further comprising the steps of:

a. admixing said conjugated linoleic acid-rich soy oil with an organic solvent;
b. filtering said oil-solvent admix through a porous cellulose membrane; and
c. collecting iodine permeate after said oil-solvent admix filters through said membrane.

6. The method of claim 5 wherein said organic solvent is miscible with said conjugated linoleic acid-rich soy oil, has a high iodine solubility, and is safe for use in food, nutraceutical and/or pharmaceutical processing.

7. The method of claim 6 wherein said organic solvent is a cyclohexane:ethanol mix with about 50% to about 68% v/v ethanol, having an iodine solubility of about 24% to about 32% w/w.

8. The method of claim 5 wherein after said step (b) of filtering said oil-solvent admix through said membrane, further comprising the steps of:
a. admixing supernatant of said oil-solvent admix with an additional about of said organic solvent to form a second oil-solvent admix;
b. filtering said second oil-solvent admix through said membrane; and
c. collecting iodine permeate after said second oil-solvent admix filters through said membrane.

9. The method of claim 5 wherein said step (b) of filtering said oil-solvent admix through said membrane is performed under hydrostatic pressure from an inert gas.

10. The method of claim 8 wherein said step (b) of filtering said second oil-solvent admix through said membrane is performed under hydrostatic pressure from an inert gas.

11. A composition, comprising:
a trans-9,trans-11 and trans-10,trans-12-conjugated linoleic acid isomer composition produced from photoisomerization of soy oil in the presence of γ-tocopherol; and
a human or animal food substance, a pharmaceutically acceptable carrier or a nutraceutically acceptable carrier.

12. The composition of claim 11 wherein said γ-tocopherol is at least 1,400 ppm γ-tocopherol.

13. The composition of claim 12 wherein said at least 1,400 ppm γ-tocopherol is approximately 1,400 ppm to approximately 1,800 ppm γ-tocopherol.

14. The composition of claim 11 wherein said conjugated linoleic acid isomer composition contains approximately 75% trans-9,trans-11- and trans-10,trans-12 positional isomers of conjugated linoleic acid.

15. A trans-,trans-conjugated linoleic acid composition derived from photoisomerization of soy oil and at least one antioxidant, said composition comprising a geometrical isomer composition having about 75% trans-9,trans-11-conjugated linoleic acid and trans-10,trans-12-conjugated linoleic acid, or a mixture thereof.

16. The trans-,trans-conjugated linoleic acid composition of claim 15 wherein said composition is a pharmaceutical, nutraceutical or human or animal food composition.

17. The trans-,trans-conjugated linoleic acid composition of claim 15 wherein said antioxidant is at least 1,400 ppm γ-tocopherol.

18. The trans-,trans-conjugated linoleic acid composition of claim 17 wherein said at least 1,400 ppm γ-tocopherol is approximately 1,400 ppm to approximately 1,800 ppm γ-tocopherol.

19. A method of treatment or prevention of obesity, said method comprising the steps of:
administering a therapeutically effective amount of a trans-9, trans-11 and trans-10,trans-12-isomer enriched conjugated linoleic acid composition produced from photoisomerization of said composition in the presence of γ-tocopherols.

20. The method of claim 19 wherein said isomer enriched conjugated linoleic acid composition is administered topically as a lotion, gel or an emulsion or administered orally as a dietary supplement or as a food ingredient.

21. The method of claim 19 wherein said isomer enriched conjugated linoleic acid composition is a pharmaceutical, nutraceutical or human or animal food composition.

* * * * *

UNITED STATES PATENT AND TRADEMARK OFFICE
CERTIFICATE OF CORRECTION

PATENT NO. : 8,809,560 B2  
APPLICATION NO. : 13/471624  
DATED : August 19, 2014  
INVENTOR(S) : Andrew Proctor et al.

Page 1 of 1

It is certified that error appears in the above-identified patent and that said Letters Patent is hereby corrected as shown below:

On the title page, item (75), amend "Reddy Yettella Yenkata Ramesh" to --Reddy Yettella Venkata Ramesh--

Signed and Sealed this  
Fourth Day of November, 2014

Michelle K. Lee  
*Deputy Director of the United States Patent and Trademark Office*